(12) United States Patent
Goodman et al.

(10) Patent No.: US 7,544,715 B2
(45) Date of Patent: Jun. 9, 2009

(54) TUMOR IMAGING COMPOUNDS

(75) Inventors: Mark M. Goodman, Atlanta, GA (US); Jonathan McConathy, Decatur, GA (US)

(73) Assignee: Emory University, Atlanta, GA (US)

( * ) Notice: Subject to any disclaimer, the term of this patent is extended or adjusted under 35 U.S.C. 154(b) by 552 days.

(21) Appl. No.: 10/507,221

(22) PCT Filed: Apr. 24, 2003

(86) PCT No.: PCT/US03/12748

§ 371 (c)(1), (2), (4) Date: Apr. 15, 2005

(87) PCT Pub. No.: WO03/093412

PCT Pub. Date: Nov. 13, 2003

(65) Prior Publication Data

US 2005/0192458 A1 Sep. 1, 2005

Related U.S. Application Data

(60) Provisional application No. 60/377,124, filed on Apr. 30, 2002.

(51) Int. Cl.
  A61K 31/195 (2006.01)
  A61K 31/19 (2006.01)
  C07C 229/00 (2006.01)
(52) U.S. Cl. .................. 514/561; 514/572; 562/574
(58) Field of Classification Search ............ None
  See application file for complete search history.

(56) References Cited

U.S. PATENT DOCUMENTS

| | | |
|---|---|---|
| 3,855,208 A | 12/1974 | Rutner et al. |
| 4,325,961 A | 4/1982 | Kollonitsch et al. |
| 4,358,434 A | 11/1982 | Tzodikov et al. |
| 4,390,517 A | 6/1983 | O'Brien et al. |
| 4,483,870 A | 11/1984 | Kollonitsch et al. |
| 4,695,588 A | 9/1987 | Kollonitsch et al. |
| 4,743,691 A | 5/1988 | Bey et al. |
| 4,760,091 A | 7/1988 | Carson et al. |
| 4,942,231 A | 7/1990 | Mertens |
| 5,227,467 A | 7/1993 | Kollonitsch et al. |
| 5,279,812 A | 1/1994 | Krstenansky et al. |
| 5,310,912 A | 5/1994 | Neumeyer et al. |
| 5,324,504 A | 6/1994 | Roger, Jr. et al. |
| 5,413,779 A | 5/1995 | Kuhar et al. |
| 5,637,759 A | 6/1997 | Hearst et al. |
| 5,698,179 A | 12/1997 | Neumeyer et al. |
| 5,808,146 A | 9/1998 | Goodman et al. |
| 5,817,776 A | 10/1998 | Goodman et al. |
| 5,853,696 A | 12/1998 | Elmaleh et al. |
| 6,344,179 B1 | 2/2002 | Goodman |
| 6,399,042 B1 | 6/2002 | Goodman |
| 2002/0099184 A1 | 7/2002 | Goodman |

FOREIGN PATENT DOCUMENTS

| | | |
|---|---|---|
| WO | WO 97/17092 | 5/1997 |
| WO | WO 97/43285 | 11/1997 |

OTHER PUBLICATIONS

Alexoff, DL et al. (1992), "Ion Chromatographic Analysis of High Specific Activity [18] FDG Preparations and Detection of the Chemical Impurity 2-Deoxy-2-chloro-D-glucose" I *Internat. J. Rad. Appl. Instr. Part A* 43(11):1313-1322.

Bergmann, ED et al. (1962), "Organic Fluorine Compounds. Part XXVII. Fluorinated α-Aminoisobutyric Acids"; *J. Chem. Soc.* 3462-3463.

Betz, AL et al. (1978), "Polarity of the Blood-Brain Barrier: Neutral Amino Acid Transport into Isolated Brain Capillaries"; *Science* 202:225-227.

Bey, P et al.(1979), "Direct Synthesis of Alpha-Halogenomethyl-Alpha-Amino Acids from the Parent Apha-Amino Acids"; *J. Org. Chem.* 44(15):2732-2742.

Blough, BE et al. (1996), "Synthesis and Transporter Binding Properties of 3β-(4'-Alkyl-, 4'-alkenyl-, and 4[1]-alkynylphenyl)nortropane-2β-carboxylic Acid Methyl Esters: Serotonin Transporter Selective Analogs" *J. Med. Chem.* 39(20):4027-4035.

(Continued)

*Primary Examiner*—Paul A Zucker
(74) *Attorney, Agent, or Firm*—Greenlee, Winner and Sullivan, P.C.

(57) ABSTRACT

The invention provides novel amino acid compounds of use in detecting and evaluating brain and body tumors. These compounds combine the advantageous properties of α-aminoisobutyric acid (AIB) analogs namely, their rapid uptake and prolonged retention in tumors with the properties of halogen substituents, including certain useful halogen isotopes such as fluorine-18, iodine-123, iodine-124, iodine-125, iodine-131, bromine-75, bromine-76, bromine-77, bromine-82, astatine-210, astatine-211, and other astatine isotopes. In addition the compounds can be labeled with technetium and rhenium isotopes using known chelation complexes. The amino acid compounds disclosed herein have a high specificity for target sites when administered to a subject in vivo. The labeled amino acid compounds are useful as imaging agents in detecting and/or monitoring tumors in a subject by Positron Emission Tomography (PET) and Single Photon Emission Computer Tomography (SPECT).

30 Claims, 3 Drawing Sheets

OTHER PUBLICATIONS

Blough, BE et al. (1997), "3β-(4-Ethyl-3-iodophenyl)nortropane-2β-carboxylic Acid Methyl Ester as a High-Affinity Selective Ligand for the Serotonin Transporter"; *J. Med. Chem.* 40(24):3861-3864.

Bodsch et al. (1988), "Biochemical and Autoradiographic Study of Cerebral Protein Synthesis with Fluorine-18 Fluorophenylalanine and Carbon-14 Fluorophenylalanine"; *J. Neurochemistry* 50(3):979-983.

Boger, DL et al. (1992), "Functional Analogs of CC-1065 and the Duocarmycins Incorporating the 9a-(Chloromethyl)-1,2,9,9a-tetrahydrocyclopropa[c]benz[e]indol-4-one ($C_2BI$) Alkylation Sunbunit: Synthesis and Preliminary DNA Alkylation Studies"; *J. Amer. Chem. Soc.* 114:9318-9327.

Buonocore, E (1992), "Comparison Of PET With Conventional Imaging Techniques"; *Clinical Positron Emission Tomography.* Mosby-Year Book Inc. St. Louis, MO, pp. 17-22.

Bussolati, O et al. (1996), "The stimulation of Na, K, Cl cotransport and of system A for neutral amino acid transport is a mechanism for cell volume increase during the cell cycle"; *The FASEB Journal* 10:920-926.

Chiotellis, E et al. (1977), "Preparation of Tc-99m Labeled Pyridoxal-Amino Acid Complexes and their Evaluation"; *Int. J. Nucl. Med. Biol.* 4(1):29-41.

Christensen, HN et al. (1983), "Synthesis and Transport applications of 3-Aminobicyclo[3.2.1]octane-3-carboxylic Acids"; *J. Med. Chem.* 16:1374-1378.

Coleman, RE. (1991), "Single Photon Emission Computed Tomography and Positron Emission Tomography in Cancer Imaging"; *Cancer* 67(4 suppl):1261-1270.

Conti, PS et al. (1986), "Tumor Imaging with Carbon-11 Labeled Alpha-Aminoisobutyric Acid (AIB) in a Patient with Advanced Malignant Melanoma"; *Eur. J. Nucl. Med.* 12:353-356.

Conti, PS (1995), "Introduction to Imaging Brain Tumor Metabolism with Positron Emmision Tomography (PET)"; *Cancer Invest.* 13(2):244-259.

Conti, PS et al. (1985), "Tumor localization of alpha-aminoisobutyric acid (AIB) in human melanoma heterotransplants"; *Eur. J. Nucl. Med.* 10:45-47.

Damhaut, P et al. (1997), "No-Carrier-Added Asymmetric Synthesis of Alpha-Methyl-Alpha-Amino Acids Labelled with Fluorine-18"; *Tetrahedron* 53(16):5785-5796.

Di Chiro et al. (1982), "Glucose utilization of cerebral gliomas measured by [$^{18}$ F] Fluorodeoxyglucose and Positron Emission Tomography"; *Neurology* (NY) 32:1323-1329.

Dunzendorfer, U et al. (1981), "Synthesis and Body Distribution of Alpha-Aminoisobutyric Acid-L-$^{11}$ C in Normal and Prostate Cancer-Bearing Rat After Chemotherapy"; *Eur. J. Nucl. Med.* 6:535-538.

Dutta, AK et al. (1996), "Structure-Activity Relationship Studies of Novel 4-[2-[Bis(4-fluorophenyl)methoxy]ethyl]-1-(3-phenylproply-piperidine Analogs: Synthesis and Biological Evaluation at the Dopamine and Serotonin Transporter Sites"; *J. Med. Chem.* 39:749-756.

Feinendegen, LE (1993), "Contributions of Nuclear Medicine to the Therapy of Malignant Tumors (editorial)"; *J. Can. Res. Clin. Oncol.* 119(6):320-322.

Fischman, AJ et al. (1997), "SPECT Imaging of Dopamine Transporter Sites in Normal and MPTP-Treated Rhesus Monkeys"; *J. Nucl. Med.* 38:144-150.

Giros, B. et al. (1996), "Hyperlocomotion and indifference to cocaine and amphetamine in mice lacking the dopamine transporter"; *Nature* 379:606-612.

Goodman, MM et al. (1994), "Synthesis and Characterization of Radioiodinated N-(3-Iodopropen-1-yl)-2β-carbomethoxy-3β-(4-chlorophenyl)tropanes: Potential Dopamine Reuptake Site Imaging Agents"; *J. Med. Chem.* 37:1535-1542.

Goodman, MM et al. *Clinical Positron Emission Tomography* Mosby Year Book, 1992, K.F. Hubner, et al., Chapter 14 "Automated Synthesis of Radiotracers for PET Applications" pp. 110-122.

Griffeth, LK et al. (1993), "Brain Metastases from Non-Central Nervous System Tumors: Evaluation with PET"; *Radiology* 186:37-44.

Hoyte, R et al. (1970), "Fluorine-18 Labeled Amino-Acids for Organic Imaging"; *J. Nucl. Med.* 11(10):633. (Abstract only).

Hume, SP et al. (1991), "Citalopram: Labelling with Carbon-11 and Evaluation in Rat as a Potential Radioligand for In Vivo PET Studies of 5-HT Re-uptake Sites"; *Nucl. Med. Biol.* 18:339-351.

Ishiwata et al. (1993), "Re-evaluation of Amino Acid PET Studies: Can the Protein Synthesis Rates in Brain and Tumor Tissues be Measured in Vivo?" *J. Nucl. Med.* 34(11):1936-1943.

Jager, PL et al. (2001), "Radiolabeled Amino Acids: Basic Aspects and Clinical Applications in Oncology"; *Nucl. Med.*, 42:432-445.

Kilbourn, MR et al. (1989), "Synthesis of Radiolabeled Inhibitors of Presynaptic Monoamine Uptake Systems: [$^{18}$ F]GBR 13119(DA),[$^{11}$ C]Nisoxetine (NE), and [$^{11}$ C]Fluoxtine (5-HT)" *J. Label. Cmpd. Radiopharm.* 26:412-414. (Symposium Abstract).

Kollonitsch et al. (1975), "Selective Flourination of Hydroxy Amines and Hydroxy Amino-Acids with Sulfur Tetrafluoride in Liquid Hydrogen Fluoride"; *J. Org. Chem.* 40(25):3808-3809.

Kubota, K et al. (1984), "Tumor detection with carbon-11-labelled amino acids"; *Eur. J. Nucl. Med.* 9:136-140.

Kung, M-P. et al. (1995), "IPT: A Novel Iodinated Ligand for the CNS Dopamine Transporter"; *Synapse* 20:316-324.

Kuntschke, D et al.(1995), "New [$^{99m}$ Tc]-Cytetrene Amine Compounds as Specific Brain Imaging Agents"; *J. Labelled Compounds and Radiopharmaceuticals* 36(2): 193-203.

Langleben, DD et al. (2000), "PET in Differentiation of Recurrent Brain Tumor from Radiation Inury"; *J. Nucl. Med.* 41:1861-1867.

Liu, S et al. (1996), "Labeling Cyclic Glycoprotein IIb/IIIa Receptor Antagonists with $^{99m}$ Tc by the Preformed Chelate Approach: Effects of Chelators on Properties of [$^{99m}$ Tc] Chelator-Peptide Conjugates"; *Bioconjugate Chem.* 7(2):196-202.

Malison, RT et al. (1995), "Striatal Dopamine Transporter Imaging in Nonhuman primates with Iodine-123-IPT SPECT"; *J. Nucl. Med.* 36:2290-2297.

Maryanoff, BE et al. (1987), "Pyrroloisoquinoline Antidepressants. In-Depth Exploration of Structure-Activity Relationships"; *J. Med. Chem.* 30:1433-1454.

Mathis, C et al. (1993), "Synthesis and Biological Evaluation of a PET Radioligand for Serotonin Uptake Sites: [F-18]5-Fluoro-6-Nitroquipazine"; *J. Nucl. Med.* 34:7P-8P. (Abstract only).

Matsushima, Y et al. (1984), "Evaluation of Technetium-99m-Labeled Amino Acids as Radiopharmaceuticals. VI. N-Pyridoxylidenehydrazine-N',N'-Diacetic Acid"; *Chem. Pharm. Bull.* 32(6):2262-2266.

Meegalla, SK et al. (1997), "Synthesis and Characterization of Technetium-99m-Labeled Tropanes as Dopamine Transporter-Imaging Agents"; *J. Med. Chem.* 40:9-17.

Monclus, M et al. (1995), "Asymmetric Synthesis of Fluorinated L-Tyrosine and *meta*-L-Tyrosines" *J. Fluorine Chem.* 70(1):39-43.

Murphy, DL et al. (1986), "Use of Serotonergic Agents in the Clinical Assessment of Central Serotonin Function" *J. Clin. Psychiatr.* 47:4(supp)9-15.

Nagren, K et al. (2000), "[N-methyl-$^{11}$ C]MeAIB, a Tracer for System A Amino Acid Transport: Preparation from [$^{11}$ C]Methyl Triflate and HPLC Metabolite Analysis of Plasma Samples After Intravenous Administration in Man"; *J. Labelled Cpd Radiopharm.* 43:1013-1021.

Niznik, HB et al. (1991), "The Dopamine Transporter is Absent in Parkinsonian Putamen and Reduced in the Caudate Nucleus"; *J. Neurochem.* 56:192-198.

Ogawa, T et al. (2993), "Cerebral Glioma: Evaluation with Methionine PET[1] "; *Radiology* 186:45-53.

Palacin, M et al. (1998), "Molecular Biology of Mammalian Plasma Membrane Amino Acid Transporters"; *Physiol. Rev.* 78:969-1054.

Posakony, JJ et al. (1999), "Progress in the Synthesis of [18-F]-Fluoroamines; Precursors to β-Selective Andrenergic Ligands"; *J. Labelled. Cmpd. Radiopharm.* 42:S527-529.

Schmall, B et al. (1987) "Imaging Studies of Patients with Malignant Fibrous Histiocytoma using C-11-Alpha-Aminoisbutyric Acid (AIB)"; *Clin. Nucl. Med* 12(1):22-26.

Schober, O et al. (1992), "Evaluation of Brain Tumors by Positron Emission Tomography"; *Radiologe* 32(6):282-289.

Shiba, K et al. (1984), "Comparitive Distribution Study of Carbon-14-Labeled Amino-Acids Glucose Analog and Precursor of Nucleic-Acid as Tumor Seeking Agents," *Radioisotopes* 33(8):526-532.

Shotwell, MA et al. (1983), "The Regulation of Neutral Amino Acid Transport in Mammalian Cells"; *Biochem. Biophys. Acta*. 737:267-284.

Shoup, TM et al. (1999), "Synthesis and Evaluation of [$^{18}$F]1-Amino-3-fluorocyclobutane-1-carboxylic Acid to Image Brain Tumors"; *J. Nucl Med*. 40:331-338.

Suehiro, M et al. (1991), "Radiosynthesis and Evaluation of N-(3-[$^{18}$F]Fluoropropyl) paroxetine as a Radiotracer for In Vivo Labeling of Serotonin Uptake Sites by PET"; *Nucl. Med. Biol*. 18:791-796.

Suehiro, M et al. (1992), "Synthesis of a Radiotracer for Studying Serotonin Uptake Sites with Positron Emission Tomography: [$^{11}$C]McN-5652-Z"; *J. Label Cmpd. Radiopharm*. 31:841-848.

Suehiro, M et al. (1993), "A PET Radiotracer for Studying Serotonin Uptake Sites: Carbon-11-McN-5652Z"; *J. Nucl. Med*. 34:120-127.

Tamemasa, O et al. (1984), "Tumor Detection with some 99m-Tc-Labeled S-Containing Amino Acids"; *Gann*. 75(5):395-402.

Taylor, JS et al. (1983), "Flourinated α-methylamino Acids as $^{19}$F NMR Indicators of Intracellular pH"; *Biophys. J*. 43(3):261-267.

Thierry, J et al. (1998), "2-Phenyl Isopropyl and t-Butyl Trichloroacetimidates: Useful Reagents for Ester Preparation of N-Protected Amino acids under Neutral Conditions"; *Tetrahedron Lett*. 39:1557-1560.

Verbruggen, AM et al. (1992), "Technetium-99m-L,L-Ethylenedicysteine: A Renal Imaging Agent. I. Labeling and Evaluation in Animals"; *J Nucl. Med*. 33(4):551-557.

Washburn, LC et al. (1979), "High-Level Production of C-11-Carboxyl-labeled Amino Acids"; in *Radiopharmaceuticals II: Proceedings 2$^{nd}$ International Symposium on Radiopharmaceuticals*, Mar. 19-22, 1979, Seattle, Washington.

Washburn, LC et al. (1979), "1-Aminocyclobutane[$^{11}$C]Carboxylic Acid, A Potential Tumor-Seeking Agent"; *J. Nucl. Med*. 20:1055-1061.

Weiland, DM et al. (1988), "NMDA Receptor Channels: Labeling of MK-801 with Iodine-125 and Fluorine-18"; *Appl. Radiat. Isotop*. 39:1219-1225.

Supplementary European Search Report, Application No. 03747599.3, Jun. 28, 2007, 2 pages.

H. N. Christensen et al., The Use of N-Methylation to Direct the Route of Mediated Transport of Amino Acids, The Journal of Biological Chemistry 240(9):3609-3616, Sep. 1965.

Wermuth C. G. (ed.), Chapter 17 of The Practice of Medicinal Chemistry, In Japanese, Translation supervised by Hiroshi Nagase, Saishin Soyaku Kagaku, first volume, Aug. 15, 1998, pp. 353-388.

Wermuth C. G. (ed.), Chapter 17: Specific Substituent Effects, In: The Practice of Medicinal Chemistry, Academic Press Limited, 1996, pp. 311-344.

McConathy et al. (2001) "Introduction of 18F at neopentyl positions via cyclic sulfamidates: Synthesis of 18F-labeled alpha, alpha-dialkyl amino acids as potential tumor imaging agents," J Labeled Cpd. Radiopharm. 44(Suppl. 1):S376-S378.

McConathy et al. (2001) "Famp and N-methyl famp: Fluorinated analogs of aminoisobutyric acid with high uptake in a rodent model of intracranial tumors," 48th Annual Meeting of the Society of Nuclear Medicine, Toronto, Canada, Jun. 23-27, 2001, Abstract No. 558.

TUMOR IMAGING COMPOUNDS

CROSS REFERENCE TO RELATED APPLICATIONS

This application is a National Stage Application of PCT International Application No. PCT/US2003/012748, filed on Apr. 24, 2003, which claims benefit of U.S. Provisional Application No. 60/377,124, filed on Apr. 30, 2002, which is incorporated herein by reference in its entirety.

The development of radiolabeled amino acids for use as metabolic tracers to image tumors using positron emission tomography (PET) and single photon emission computed tomography (SPECT) has been underway for two decades. Although radiolabeled amino acids have been applied to a variety of tumor types, their application to intracranial tumors has received considerable attention due to potential advantages over other imaging modalities. After surgical resection and/or radiotherapy of brain tumors, conventional imaging methods such as CT and MRI do not reliably distinguish residual or recurring tumor from tissue injury due to the intervention and are not optimal for monitoring the effectiveness of treatment or detecting tumor recurrence [Buonocore, E (1992), *Clinical Positron Emission Tomography*. Mosby-Year Book, Inc. St. Louis, Mo., pp 17-22; Langleben, DD et al. (2000), *J. Nucl. Med.* 41:1861-1867].

The leading PET agent for diagnosis and imaging of neoplasms, 2-[$^{18}$F]fluorodeoxyglucose (FDG), also has limitations in the imaging of brain tumors. Normal brain cortical tissue shows high [$^{18}$F]FDG uptake as does inflammatory tissue which can occur after radiation or surgical therapy; these factors can complicate the interpretation of images acquired with [$^{18}$F]FDG [Griffeth, LK et al. (1993), *Radiology*. 186:37-44; Conti, PS (1995)].

A number of reports indicate that PET and SPECT imaging with radiolabeled amino acids better defines tumor boundaries within normal brain than CT, MRI or [$^{18}$F]FDG, allowing better planning of treatment [Ogawa, T et al. (1993), *Radiology*. 186: 45-53; Jager, PL et al. (2001), *Nucl. Med,* 42:432-445]. Additionally, some studies suggest that the degree of amino acid uptake correlates with tumor grade, which could provide important prognostic information [Jager, PL et al. (2001) *J. Nucl. Med.* 42:432-445].

A number of amino acids, including [$^{11}$C]α-aminoisobutyric acid (AIB), L-[$^{11}$C]methionine (Met), L-[$^{18}$F]fluoro-α-methyl tyrosine, O-(2-[$^{18}$F]fluoroethyl)tyrosine and trans-1-amino-3-[$^{18}$F]fluorocyclobutyl-1-carboxylic acid (FACBC), have been successfully used for PET tumor imaging in humans [Jager, PL et al. (2001), *J. Nucl. Med.* 42:432-445; Shoup, TM et al. (1999), *J. Nucl. Med.* 40:331-338]. [$^{18}$F] FACBC has been disclosed in U.S. Pat. Nos. 5,808,146 and 5,817,776, incorporated herein by reference. AIB is a nonmetabolized α,α-dialkyl amino acid that is actively transported into cells primarily via the A-type amino acid transport system. System A amino acid transport is increased during cell growth and division and has also been shown to be upregulated in tumor cells [Palacín, M et al. (1998), *Physiol. Rev.* 78: 969-1054; Bussolati, O et al. (1996), *FASEB J.* 10:920-926]. Studies of experimentally induced tumors in animals and spontaneously occurring tumors in humans have shown increased uptake of radiolabeled AIB in the tumors relative to normal tissue [Conti, PS et al. (1986), *Eur. J. Nucl. Med.* 12:353-356; Uehara, H et al. (1997), *J. Cereb. Blood Flow Metab.* 17:1239-1253]. The N-methyl analog of AIB, N-MeAIB, shows even more selectivity for the A-type amino acid transport system than AIB [Shotwell, MA et al. (1983), *Biochim. Biophys. Acta.* 737:267-84]. N-MeAIB has been radiolabeled with carbon-11 and is metabolically stable in humans [Någren, K et al. (2000), *J. Labelled Cpd. Radiopharm.* 43:1013-1021].

Disclosed herein are fluorinated analogs of AIB suitable for labeling with $^{18}$F and use in PET imaging. These agents are expected to demonstrate metabolic stability in vivo due to their α,α-dialkyl branching and to have the potential for remote distribution due to the 110 minute is half-life of $^{18}$F versus 20 minutes for $^{11}$C. Specifically exemplified are the synthesis, radiolabeling and biological evaluation of two exemplary compounds of the invention, 2-amino-3-fluoro-2-methylpropanoic acid (FAMP, 5a) and 3-fluoro-2-methyl-2-(methylamino)propanoic acid (N-MeFAMP, 5b), fluorinated analogs of AIB and N-methyl AIB respectively. The dominant mechanism of cellular uptake of these radiotracers by 9L gliosarcoma cells has been determined in vitro using inhibitors of amino acid transport. Tissue distribution studies in normal and 9L gliosarcoma tumor-bearing rats have been carried out after intravenous administration of [$^{18}$F]5a and [$^{18}$F]5b, and the tumor uptake of radioactivity was compared to uptake in normal brain for both compounds.

SUMMARY OF THE INVENTION

The invention provides novel amino acid compounds of use in detecting and evaluating brain and body tumors. These compounds combine the advantageous properties of α-aminoisobutyric acid (AIB) analogs namely, their rapid uptake and prolonged retention in tumors with the properties of halogen substituents, including certain useful halogen isotopes such as fluorine-18, iodine-123, isodine-124, iodine-125, iodine-131, bromine-75, bromine-76, bromine-77, bromine-82, astatine-210, astatine-211, and other astatine isotopes. In addition the compounds can be labeled with technetium and rhenium isotopes using known chelation complexes.

In one aspect, the invention features amino acid compounds that have a high specificity for target sites when administered to a subject in vivo. Preferred amino acid compounds show a target to non-target ratio of at least 5:1, are stable in vivo and substantially localized to target within 1 hour after administration. Especially preferred amino acid compounds include [$^{18}$F]FAMP, ([$^{18}$F]5a) and [$^{18}$F]N-MeFAMP, ([$^{18}$F]5b).

In another aspect, the invention features pharmaceutical compositions comprised of an α-amino acid moiety attached to either a four, five, or a six member carbon-chain ring. In addition, the invention features analogs of α-aminoisobutyric acid.

In a further aspect, the invention features amino acid compounds further comprising an imaging agent and uses for the compounds in detecting and/or monitoring tumors in a subject. In one embodiment, the amino acid compound imaging agent is administered in vivo and monitored using a means appropriate for the label. Preferred methods for detecting and/or monitoring an amino acid compound imaging agent in vivo include Positron Emission Tomography (PET) and Single Photon Emission Computer Tomography (SPECT).

Compounds of the invention include fluoro-, bromo- or iodo-substituted cyclobutyl, cyclopentyl, cyclohexyl amino acids, or singly unsaturated cyclic homologs thereof, or methylenyl fluoride or iodide-substituted analogs, or fluoro- or iodo-substituted isobutyl amino acids. The substituted compounds belong to the following generic formula:

where $R_1$ is X, or $R_3$ $R_2$ is H or $R_3$ if $R_1$ is $R_3$.

such that $R_3$ is formed,
$R_4$ is $-(C_kH_{2k+1})$, $-(C_kH_{2k-1})$ or $-(C_kH_{2k-3})$
And where a is 1 to 5,
x is 0 or 1,
y is 1 or 2,
z is 1, 2, 3 or 4 and z>y if y is 2,
q is 1 or 0 if n is 1 and j is 0,
n is 1 or 2, but 0 if m is 0,
m is 0 or 1,
j is 0 or 1,
k is 1-5, and
X is $^{18}$F, $^{123}$I, $^{124}$I, $^{125}$I, $^{131}$I, $^{75}$Br, $^{76}$Br, $^{77}$Br, $^{82}$Br, or At Non-cyclic, but sterically similar compounds of the invention have the following generic formula:

where $R_1$ is X or X—CH=CH—, a is 1 to 5,
and X is $^{131}$I, $^{123}$I, $^{124}$I, $^{125}$I, $^{18}$F, $^{75}$Br, $^{76}$Br, $^{77}$Br, $^{82}$Br, or At,
$R_4$ is $-(C_kH_{2k+1})$, $-(C_kH_{2k-1})$, or $-(C_kH_{2k-3})$, and
$R_2$ is $-(C_kH_{2k+1})$, $-(C_kH_{2k-1})$, or $-(C_kH_{2k-3})$
k is 1-5.

The compounds of the invention are useful as tumor-binding agents and as NMDA receptor-binding ligands, and in radio-isotopic form are especially useful as tracer compounds for tumor imaging techniques, including PET and SPECT imaging. Where X is At, the compounds have utility for radio-therapy, since At isotopes are α-emitters. In order to synthesize the compounds to maximize a useful lifetime for short-lived isotopes, and to maximize yield and purity, specialized, non-standard routes had to be devised, as described.

The cyclic and non-cyclic compounds of the invention, can be labeled with Technetium or Rhenium. Technetium-99m, Rhenium 186 and Rhenium 188 are known to be useful radionuclides for SPECT imaging. The cyclic and non-cyclic amino acids of the invention are joined to a Tc-99m or Re186 or Re 188 metal cluster through a 4-6 carbon chain which can be saturated or possess a double or triple bond. The Tc-99m metal cluster can be, for example, an alkylthiolato complex, a cytectrene or a hydrazino nicotinamide complex (HYNIC), a cyclopentadienetricarbonyl or an N287 chelate. The linking structure can be $R_5$ (replacing R3) in the foregoing diagram where $R_5$ is Z-$(CH_2)_a$—$CH_b$—CH, where a is 1, 2 or 3, b is 0, 1 or 2, and Z is an alkylthiolato-Tc or Re complex, a Tc- or Re-cytectrene or a Tc- or Re-HYNIC complex or other Tc or Re chelate as known in the art. When a structure is shown with To of Tc$^{99m}$, it will be understood to also illustrate an equivalent structure having Re 186 or Re 188 substituted for the Tc isotope.

Examples of the [$^{99m}$Tc] or Re-labeled compounds of the invention are:

where R is where a is 1, 2 or 3
b is 0,1 or 2
x is 0 or 1
y is 1 or 2
z is 1, 2, 3 or 4 and x>y if y is 2,
q is 1 or 0
$R_4$ is $-(C_kH_{2k+1})$, $-(C_kH_{2k-1})$, or $-(C_kH_{2k-3})$, where k is 1-5.

where $R_1$ is Z, a is 1 to 5,
and $R_4$ is $-(C_kH_{2k+1})$, $-(C_kH_{2k-1})$, or $-(C_kH_{2k-3})$, and
$R_2$ is $-(C_kH_{2k+1})$, $-(C_kH_{2k-1})$, or $-(C_kH_{2k-3})$
k is 1-5.
Z is

-continued $M = {}^{99m}Tc$ where b is 0, 1 or 2
x is 0 or 1
y is 1 or 2
z is 1, 2, 3, or 4 and x>y if y is 2,
q is 0 or 1

M = Tc or Re

DETAILED DESCRIPTION OF THE INVENTION

In general the terms and phrases used herein have their art-recognized meaning, which can be found by reference to standard texts, journal references and contexts known to those skilled in the art.

Compounds of the invention provide substantially improved PET and SPECT imaging for areas of the body having malignant tumors, especially tumors of the brain. The labeled compounds disclosed herein not only provide longer useful half-lives but also exhibit greater binding specificity for the target tissue/cells with low non-specific binding for the non-target tissues or cells.

Specifically exemplified herein are the synthesis, the results of the amino acid uptake assays and the in vivo evaluation in normal rats and a rodent tumor model of two fluorinated analogs of α-aminoisobutyric acid (AIB), 2-amino-3-fluoro-2-methylpropanoic acid (FAMP) and 3-fluoro-2-methyl-2-(methylamino)propanoic acid (N-MeFAMP) radiolabled with fluorine-18.

The key steps in the synthesis of both [$^{18}$F]FAMP and [$^{18}$F]N-MeFAMP involved the preparation of cyclic sulfamidate precursors. Radiosyntheses of both compounds via no-carrier-added nucleophilic substitution provided high yields (>78% decay-corrected) in high radiochemical purity (>99%).

Amino acid transport assays using 9L gliosarcoma cells demonstrated that both compounds are substrates for the A-type amino acid transport system, with [$^{18}$F]N-MeFAMP showing higher specificity than [$^{18}$F]FAMP for A-type transport. Tissue distribution studies in normal Fisher rats and Fisher rats implanted intracranially with 9L gliosarcoma tumor cells were also performed as described below. At 60 minutes postinjection, the tumor versus normal brain ratio of radioactivity was 36:1 in animals receiving [$^{18}$F]FAMP and 104:1 in animals receiving [$^{18}$F]N-MeFAMP. These results indicate that both [$^{18}$F]FAMP and [$^{18}$F]N-MeFAMP are promising imaging agents for the detection of intracranial neoplasm via positron emission tomography.

Compounds 5a and 5b are fully described as examples of compounds of the invention. The syntheses of non-radioactive 5a and 5b are shown in Scheme 1. For 5a, the aminonitrile 1 was prepared from fluoroacetone using a Strecker-type reaction. To facilitate purification, the carbamate 2 was prepared by treating the crude product of the acid hydrolysis of 1 with di-tert-butyl dicarbonate followed by flash chromatography. The amino acid 5a was obtained as its salt in analytically pure form by treating 2 with aqueous HCl. Compound 2 could also be obtained by treating 14a (see Scheme 4 for structure) with tetrabutylammonium fluoride and derivatizing the crude amino acid using di-tert-butyl dicarbonate. Preparation of 5b was performed starting with the carbamate 2. Treatment of 2 with tert-butyl-2,2,2-trichloroacetamidate under neutral conditions [Thierry, J et al. (1998), *Tetrahedron Lett.* 39:1557-1560] provided the N-tert-butoxycarbonyl (N-Boc) ester 3 which was alkylated with methyl iodide and sodium hydride in DMF to yield 4. Deprotection of 4 in aqueous HCl provided amino acid 5b as its salt. Although synthesis of 5a and 5b via the aminonitrile intermediate was straightforward, this strategy was not amenable to radiosynthesis of [$^{18}$F]5a and [$^{18}$F]5b.

Initial attempts to prepare [$^{18}$F]5a from a methanesulfonyl ester precursor failed due to lack of $^{18}$F incorporation into the molecule, presumably because of the low reactivity of the β-carbon due to its neopentyl character. As an alternative, cyclic sulfamidates were attractive precursors because they have been used to prepare a number of $^{18}$F radioligands and non-radioactive α,α-disubstituted amino acid derivatives including 3-fluoro-2-(4-methoxybenzylamino)-2-methylpropanoic acid methyl ester [Weiland, DM et al. (1988), *Appl. Radiat. Isotop.* 39:1219-1225; Van Dort, ME et al. (1995), *J. Med. Chem.* 38:810-815; Posakony, JJ et al. (1999), *J. Labelled Cmpd. Radiopharm.* 42: S527-529]. However, there are currently no literature reports of cyclic sulfamidate formation from primary amines. While this did not pose a problem for the synthesis of [$^{18}$F]5b which contains a secondary amine, in the case of [$^{18}$F]5a it was necessary to utilize an amino substituent which was suitable for cyclic sulfamidate formation but could be readily removed during radiosynthesis (see below). For both radiotracers, the key steps in the preparation of the precursors for radiolabeling involved the synthesis of secondary aminoalcohols which could be converted to cyclic sulfamidates.

The α-methyl serine derivative 8 served as a common intermediate in the syntheses of [$^{18}$F]5a and [$^{18}$F]5b and was prepared as shown in Scheme 2. Treatment of 3-benzyloxypropanone with a buffered ammonium carbonate and potassium cyanide solution led to the formation of the hydantoin 6. Alkaline hydrolysis of the hydantoin followed by treatment of the crude amino acid with di-tert-butyl dicarbonate gave the N-Boc acid 7. The t-butyl ester 8 was prepared from 7 using t-butyl-2,2,2-trichloracetimidate under neutral conditions [Thierry, J et al. (1998), *Tetrahedron Lett.* 39, 1557-1560].

The synthesis of the aminoalcohols 12a and 12b is depicted in Scheme 3. To prepare 12a, the alcohol 9 was obtained from the catalytic hydrogenolysis of the benzyl ether 8. The bis(4-methoxyphenyl)methyl group, also known as 4,4'-dimethoxybenzhydryl (DMB), was incorporated because it provided a secondary amine for cyclic sulfamidate formation but could be rapidly removed under acidic conditions [Hanson, RW et al. (1965), *J. Chem. Soc.* 7285-7297]. This arrangement permitted N-dealkylation, hydrolysis of the sulfamate obtained from nucleophilic ring opening, and hydrolysis of the t-butyl ester in a single step after incorporation of $^{18}$F. Selective removal of the Boc protecting group of 9 in the presence of the tert-butyl ester was achieved with p-toluenesulfonic acid by modifying the procedure reported by [Goodacre, J et al. (1975), *Tetrahedron Lett.* 42:3609-12]. While the reaction did not proceed at 40° C. even with prolonged reaction times (>4 days), the desired intermediate was obtained rapidly when the solvent was removed under reduced pressure at 40° C. The crude amino ester from this procedure was monoalkylated with bis(4-methoxyphenyl) chloromethane to provide 12a.

As shown in Scheme 3, the aminoalcohol 12b was also prepared from compound 8. First, 8 was treated with methyl iodide and sodium hydride in DMF to afford the N-methyl derivative 10 in quantitative yield. Catalytic hydrogenolysis of 10 provided the alcohol 11, which was then converted to 12b with p-toluenesulfonic acid as previously described.

Scheme 4 depicts the formation of the cyclic sulfamidate precursors 14a and 14b and subsequent radiolabeling to produce the amino acids [$^{18}$F]5a and [$^{18}$F]5b. The aminoalcohols 12a and 12b were reacted with thionyl chloride in the presence of triethylamine to form cyclic sulfamidites 13a and 13b. Oxidation using sodium periodate with catalytic ruthenium (IV) oxide provided 14a and 14b from 13a and 13b, respectively. The precursors 14a and 14b are stable for at least 6 months when stored at −10° C.

Initial attempts to synthesize [$^{18}$F]5a via nucleophilic substitution of the methyl sulfonyl ester of 9 did not demonstrate measurable $^{18}$F incorporation after prolonged heating. In contrast the cyclic sulfamidate precursor 14a provided an average 78% decay corrected yield (n=4 runs) of [$^{18}$F]5a in over 99% radiochemical purity. Likewise, treatment of 14b under the same conditions gave an average 85% decay-corrected yield (n=3 runs) of [$^{18}$F]5b in over 99% radiochemical purity. The radiolabeled amino acids were prepared in a one-pot synthesis by treating the precursor 14a or 14b with no-carrier-added [$^{18}$F]fluoride at 85° C. for 20 minutes followed by acid hydrolysis at 85° C. for 10 minutes. The reaction mixture was then passed through a column containing ion-retardation resin followed by alumina and C-18 SepPaks®. The eluted fractions were pH 6-7 and suitable for direct use in the rodent studies. In a representative synthesis, a total of 76 mCi of [$^{18}$F]5b at EOS was obtained from 166 mCi of $^{18}$F (end of bombardment, EOB) in a synthesis time of approximately 90 minutes.

While the specific activities of [$^{18}$F]5a and [$^{18}$F]5b were not determined directly, the maximum amount of unlabeled material in the final product arising from the precursors is about 1 mg in each case. Based on a 100 mCi yield at the end of synthesis (EOS), the minimum ratio of radiotracer to unlabeled material for both [$^{18}$F]5a and [$^{18}$F]5b is 1 mCi per 10 g of unlabeled material. This amount of unlabeled material is comparable to the amount present in doses of [$^{18}$F]FDG which also contain non-radioactive material arising from the triflate precursor of [$^{18}$F]FDG [Alexoff, DL et al. (1992), *Internat. J. Rad. Appl. Instr. Part A.* 43: 313-22]. In doses of [$^{18}$F]FDG the majority of unlabeled material is comprised of glucose and mannose, both of which are not toxic. In the case of [$^{18}$F]5a and [$^{18}$F]$_5$b, the potential toxicity of the unlabeled material present in doses must be evaluated prior to the use of these compounds in human studies.

To test that [$^{18}$F]5a and [$^{18}$F]5b enter cells predominantly via the A-type amino acid transport system, amino acid uptake assays using cultured 9L gliosarcoma cells in the presence and absence of two well-described inhibitors of amino acid transport were performed. N-MeAIB is a selective competitive inhibitor of the A-type amino acid transport system while 2-amino-bicyclo[2.2.1]heptane-2-carboxylic acid (BCH) is commonly used as an inhibitor for the sodium-independent L-type transport system, although this compound also competitively inhibits amino acid uptake via the sodium-dependent $B^{0,+}$ and $B^0$ transport systems [Palacin, M et al. (1998), *Physiol. Rev.* 78: 969-1054]. The A- and L-type amino acid transport systems have been implicated in the in vivo uptake of radiolabeled amino acids used for tumor imaging [Jager, PL, et al. (2001), *Nucl. Med.,* 42:432-445; Uehara, H et al. (1997), *J. Cereb. Blood Flow Metab.* 17:1239-1253].

Figure 1:
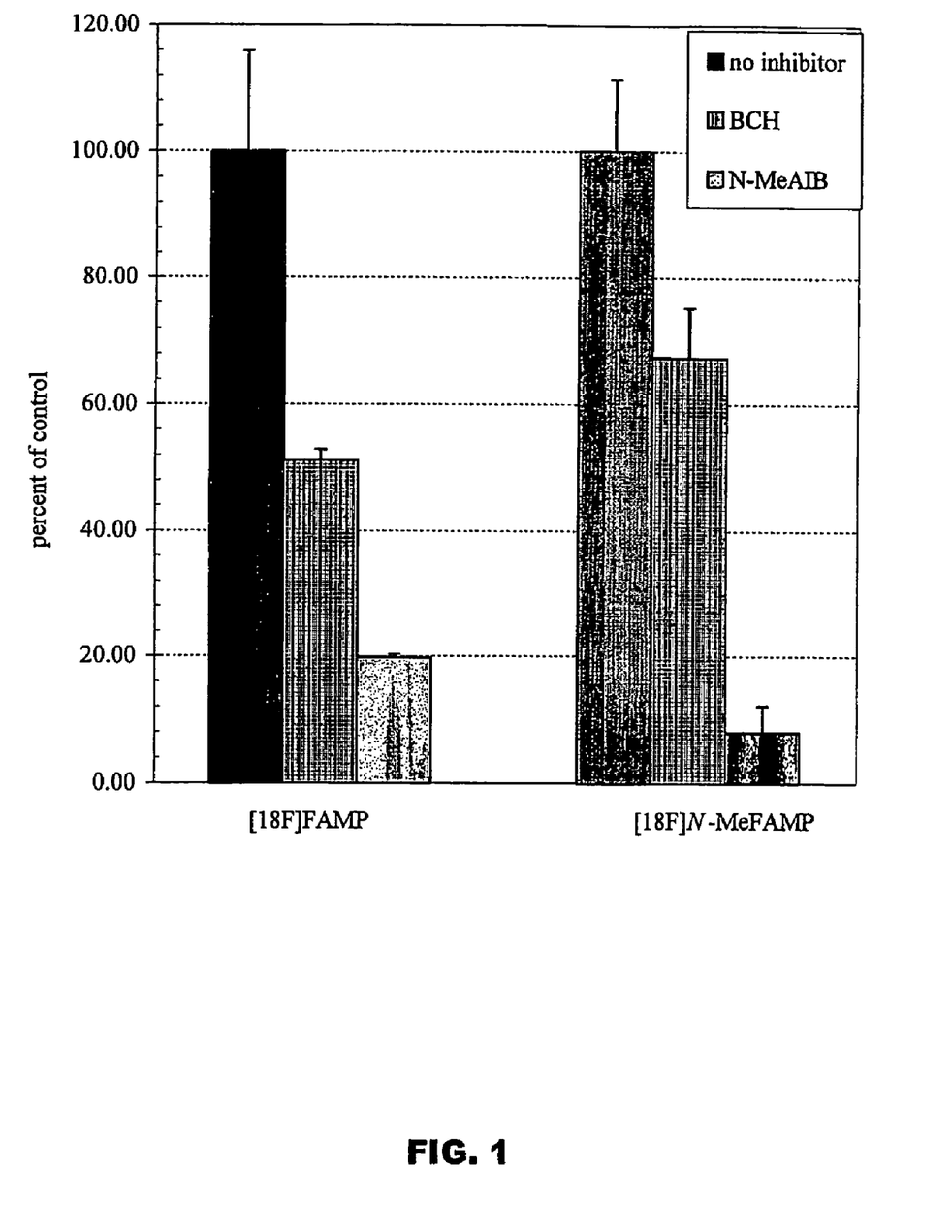
FIG. 1 shows that the uptake of [$^{18}$F]FAMP (5a) and [$^{18}$F]N-MeFAMP (5b) were inhibited by BCH and N-MeAIB in 9L gliosarcoma cells. Values are expressed as percent of control uptake (no inhibitor). Uptake was determined after 30 minutes and normalized for dose and number of cells. P-values represent comparisons of uptake in the presence of inhibitor to control uptake for each radiotracer (1-way ANOVA). *=p<0.05, **=p<0.01. Bars indicate standard error.

In the absence of inhibitors, both [$^{18}$F]5a and [$^{18}$F]5b showed similar levels of uptake in 9L gliosarcoma cells, with intracellular accumulations of 0.43% and 0.50% of the initial dose per million cells after 30 minutes of incubation, respectively. To facilitate the comparison of the effects of the inhibitors, the data were expressed as percent uptake relative to the control condition (no inhibitor) as shown in FIG. 1. In the case of [$^{18}$F]5a, BCH blocked 48% of the uptake of activity relative to controls while N-MeAIB blocked 80% of uptake relative to controls. The reduction of uptake of [$^{18}$F]5a by both BCH and N-MeAIB compared to controls was statistically significant ($p<0.05$, $p<0.01$ respectively by 1-way ANOVA). The magnitude of uptake inhibition of [$^{18}$F]5a by BCH was less than that observed with N-MeAIB but this difference between inhibitors did not reach statistical significance in this experiment.

In assays employing [$^{18}$F]5b, BCH inhibited 33% of uptake of activity compared to controls while N-MeAIB blocked 88% of uptake compared to controls. Only the reduction of uptake of [$^{18}$F]5b by N-MeAIB was significantly different from control uptake ($p<0.01$ by 1-way ANOVA), although a trend towards reduction was observed with BCH. Also, N-MeAIB reduced uptake of [$^{18}$F]5b to a greater extent than BCH ($p<0.05$ by 1-way ANOVA).

Taken together, these inhibition studies indicate that [$^{18}$F] 5a and [$^{18}$F]5b are substrates for the A-type amino acid transport system in 9L gliosarcoma cells based on the inhibition of uptake of both compounds in the presence of N-MeAIB. Additionally, [$^{18}$F]5a is also a substrate in vitro for at least one non-A transport system, possibly system L, based on the inhibition of uptake by BCH. The data indicate that [$^{18}$F]5b is a more selective substrate for the A-type amino transport system than [$^{18}$F]5a, consistent with the increased selectivity of N-MeAIB for A-type transport relative to AIB [Shotwell, MA et al. (1983), *Biochim. Biophys. Acta.* 737:267-284; Christensen, HN et al. (1983) *J. Med. Chem.* 26:1374-1378]. Because [$^{18}$F]5a and [$^{18}$F]5b were evaluated as racemic mixtures, it is possible that the enantiomers of these compounds differ in their specificity for the various amino acid transport systems. A more detailed analysis of the biological transport properties of these radiotracers and their single enantiomers in a panel of other tumor cell lines is in progress.

The results of the biodistribution studies with [$^{18}$F]5a in normal rats are presented in Table I. At 5 minutes after tail vein injection of [$^{18}$F]5a, both the pancreas and the kidneys showed significantly higher uptake of radioactivity than the other tissues studied (p<0.001 by 1-way ANOVA), with 3.46% and 6.36% of the injected dose per gram of tissue (% ID/g), respectively. The activity in these tissues remained above the activity in other tissues (p<0.001 by 1-way ANOVA at all time points), with 2.48% ID/g in the pancreas and 2.97% ID/g in the kidneys at 120 minutes. The liver showed moderate uptake of activity, with 0.65% ID/g at 5 minutes which decreased to 0.48% ID/g after 120 minutes. Other tissues studied, including heart, lung, bone, blood, muscle, and testis, showed relatively low uptake of radioactivity at 5 minutes (<0.55% ID/g) which decreased over the course of the two hour study. The brain showed the lowest uptake of radioactivity, with approximately 0.05% ID/g at all time points.

The results of the biodistribution study with [$^{18}$F]5b in normal rats were very similar to those obtained with [$^{18}$F]5a. These results for [$^{18}$F]5b are depicted in Table II. The highest uptake was observed in the pancreas and the kidneys with 2.73% ID/g and 8.12% ID/g respectively at 5 minutes. As with [$^{18}$F]5a, the brain uptake of activity was very low, with approximately 0.04% ID/g in the brain at all time points. The low brain uptake of these compounds is consistent with the observation that the A type amino transport system is not present at the intact blood-brain barrier (BBB) [Betz, AL et al. (1978), *Science.* 202:225-227]. The lack of significant accumulation of radioactivity in bone indicates that significant in vivo defluorination resulting from metabolism did not occur with either compound during the two hour studies.

The data obtained from normal rats with both [$^{18}$F]5a and [$^{18}$F]5b are similar to the reported distributions of [$^{11}$C]AIB in rats [Dunzendorfer, U et al. (1981), *Eur. J. Nucl. Med.* 6:535-538] and [$^{14}$C]AIB in mice, [Conti, PS et al. (1985), *Eur. J. Nucl. Med.* 10:45-47] suggesting that these amino acids have similar transport mechanisms in vivo. This observation is consistent with the A-type transport observed for both [$^{18}$F]5a and [$^{18}$F]5b in vitro. In healthy Copenhagen rats, the uptake of [$^{11}$C]AIB at 60 minutes was highest in the kidneys and pancreas, with 10.3 and 6.0 mean relative concentrations (mean RC, calculated from the dose fraction in the tissue divided by tissue weight multiplied by body weight), respectively. In contrast, the brain had the lowest mean RC of [$^{11}$C]AIB with a value of 0.2. In nude Swiss mice bearing human melanoma transplants that received doses of [$^{14}$C]AIB, similar results were obtained. The highest mean RCs were observed in the kidneys and pancreas at 60 minutes, with values of 3.4 and 8.6 respectively, while the brain had the lowest mean RC of organs studied with a value of 0.23. As with [$^{18}$F]$_5$a and [$^{18}$F]5b, the uptake of radioactivity in the pancreas and kidneys was rapid in these studies of AIB biodistribution, with mean RCs in both tissues greater than 1.8 within 5-15 minutes post-injection. In both studies of AIB, moderate liver uptake of activity was observed, while the mean RC in blood and muscle was low at 60 minutes.

High pancreatic uptake of radioactivity has been reported for a number of other $^{11}$C-labeled amino acids in rats, including L-[$^{11}$C]methionine, L-[$^{11}$C]leucine, and 1-aminocyclopentane-1-[$^{11}$C]carboxylic acid [Kubota, K et al. (1984), *Eur. J. Nucl. Med.* 9:136-140]. The pancreatic uptake ranged from approximately 3% ID/g to 5% ID/g at 60 minutes in this study of these compounds. Similarly, [$^{18}$F]FACBC showed 3.4% HD/g at 60 minutes in normal Fischer rats. The similarity between the biodistribution patterns of [$^{18}$F]5a, [$^{18}$F]5b and radiolabeled AIB, and in particular the high pancreatic and low brain uptake of radioactivity, prompted us to evaluate these compounds in tumor-bearing rats.

The tissue distribution of radioactivity after tail vein injection of [$^{18}$F]5a in the normal tissues of tumor-bearing rats was similar to that seen in normal rats and is presented in Table III. Tumor uptake of radioactivity at 5, 60 and 120 minutes after injection was 0.91, 1.96 and 1.87% ID/g, respectively, while uptake in normal brain tissue contralateral to the tumor was approximately 0.05% ID/g at each time point. The higher uptake of activity by the tumor versus normal brain was statistically significant at each time point (p<0.001 at 5 minutes and 60 minutes, p<0.003 at 120 minutes by two-tailed paired t-tests). The resulting ratios of tumor uptake to normal brain uptake were 26:1, 36:1 and 37:1 at 5, 60 and 120 minutes, respectively.

The results from the same study conducted with [$^{18}$F]5b in tumor-bearing rats are summarized in Table IV and demonstrated tumor uptake of 1.29, 2.28 and 1.94% ID/g at 5, 60 and 120 minutes post-injection, respectively. At each time point, the higher uptake of activity in the tumor versus normal brain tissue was statistically significant (p<0.02 at 5 minutes, p<0.001 at 60 minutes and 120 minutes by two-tailed paired t-tests). The ratios of tumor uptake to normal brain uptake at 5, 60 and 120 minutes obtained with [$^{18}$F]5b were 40:1, 104:1 and 97:1, respectively. Due to the relatively long intervals between time points, it is possible that the highest tumor to brain ratio was not observed for [$^{18}$F]5a or [$^{18}$F]5b. Imaging studies in non-human primates and in human cancer patients will provide more detailed information regarding the biodistribution and kinetics of tracer uptake in normal and neoplastic tissue.

For both [$^{18}$F]5a and [$^{18}$F]5b, the ratios of tumor to brain uptake of activity are higher than those reported for [$^{18}$F]FDG and trans-[$^{18}$F]FACBC in the same rodent tumor model [Shoup, TM et al. (1999), *J. Nucl. Med.* 40:331-338]. In the case of [$^{18}$F]FDG, the tumor to brain ratio was 0.8:1 at 60 minutes with 1.30% ID/g in normal brain and 1.05% ID/g in the tumor tissue, demonstrating the high levels of [$^{18}$F]FDG uptake in normal brain tissue. At 60 minutes post-injection, trans-[$^{18}$F]FACBC showed a 7:1 tumor to brain ratio with 1.72% ID/g in tumor tissue versus 0.26% ID/g in normal brain. A similar ratio of tumor to brain uptake of radiotracer was seen with trans-[$^{18}$F]FACBC in a PET scan of a human volunteer with biopsy-confirmed glioblastoma multiforme (6:1 ratio at 20 minutes post-injection), suggesting that this rodent model is useful in predicting imaging properties of radiolabeled amino acids in human patients with brain tumors.

As in the normal rats receiving [$^{18}$F]5a or [$^{18}$F]5b, high levels of uptake occurred in the pancreas and kidneys of the tumor-bearing rats. Additionally, both compounds had high uptake in tumor tissue but relatively low uptake in other tissues examined including heart lung, muscle, liver, bone and testis. Interestingly, [$^{18}$F]FACBC showed lower uptake in the kidneys in the same animal model (0.60% ID/g at 60 minutes), which may reflect less reuptake from the glomerular filtrate, but higher uptake in the liver (1.70% ID/g at 60 minutes) [Shoup, TM et al. (1999), *J. Nucl. Med.* 40:331-338]. Based on the rodent data, the pancreas, kidneys and bladder would be predicted to bear the highest dosimetry burden in human studies employing [$^{18}$F]5a or [$^{18}$F]5b. The low uptake in other normal tissues suggests that both [$^{18}$F]5a and [$^{18}$F]5b might be suitable for imaging tumors exhibiting high uptake of these amino acids in locations other than the brain. For example, the tumor to muscle ratios obtained at 60 minutes were 6.3:1 for [$^{18}$F]5a and 12:1 for [$^{18}$F]5b, while ratios of 5.3:1 for [$^{18}$F]FDG and 4.2:1 for trans-[$^{18}$F]FACBC were observed at this time point [Shoup, TM et al. (1999), *J. Nucl. Med.* 40:331-338]. Because both [$^{18}$F]5a and [$^{18}$F]5b were evaluated as racemic mixtures, it is possible that the single enantiomers of [$^{18}$F]5a and [$^{18}$F]5b would exhibit different biodistribution profiles. If one enantiomer has superior in vivo properties for tumor imaging, using it would be advantageous in terms of both radiation dosimetry and interpretation of tissue uptake of radioactivity. The isolation and evaluation of the R and S enantiomers of both [$^{18}$F]a and [$^{18}$F]5b are underway.

Figure 2A:
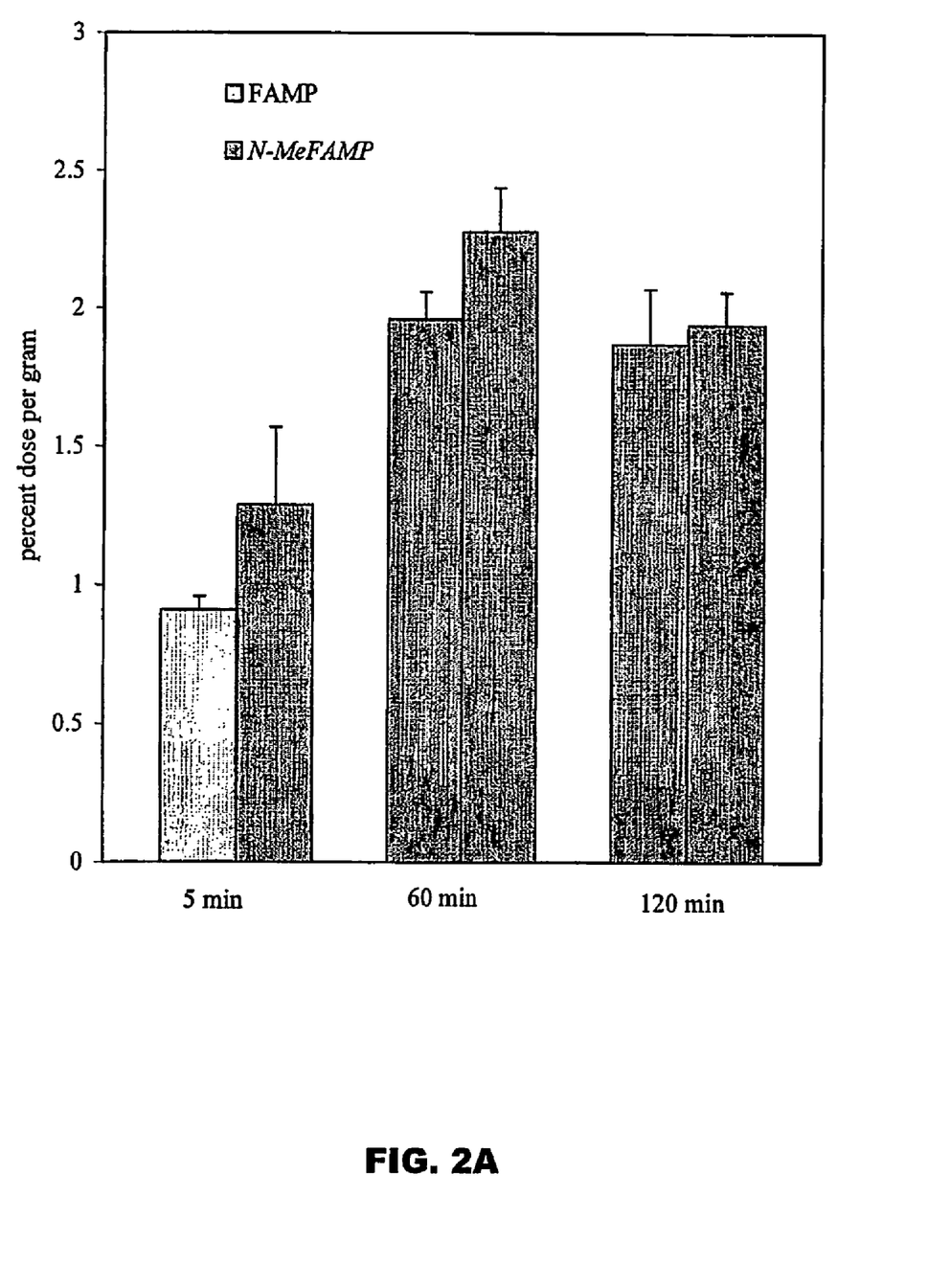
FIGS. 2A-2B are comparisons of activity in tumor tissue (FIG. 2A) and normal brain (FIG. 2B) after injection of [$^{18}$F]FAMP (5a) and [$^{18}$F]N-MeFAMP (5b). Tissues were compared at each time point by 2-tailed t-test. No significant differences in tumor uptake, but were detected. Bars indicate standard error.
Figure 2B:
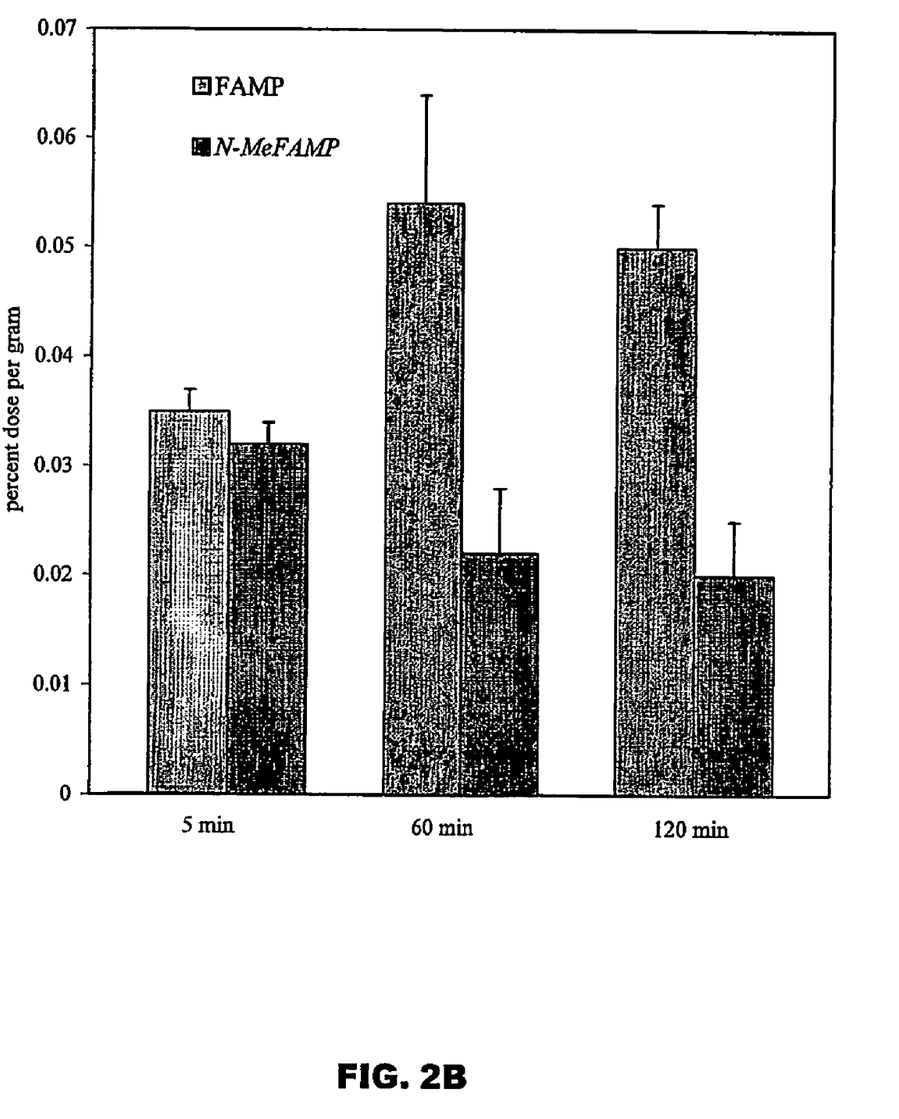

A comparison of the uptake of radioactivity in tumor tissue and brain tissue after [$^{18}$F]5a and [$^{18}$F]5b administration is depicted in FIGS. 2A and 2B. The higher ratios of tumor to brain uptake obtained with [$^{18}$F]5b versus [$^{18}$F]5a appear to be due to lower brain uptake of activity with [$^{18}$F]5b rather than higher tumor uptake of activity. No statistically significant differences were detected between the two compounds when comparing the uptake of activity in the tumor at the three time points studied (see FIG. 2A). This observation is consistent with the amino acid uptake assay in which cultured 9L gliosarcoma cells accumulated [$^{18}$F]5a and [$^{18}$F]5b in similar amounts. However, at both 60 and 120 minutes post-injection, the uptake of radioactivity in the normal brain tissue of rats receiving [$^{18}$F]5b was significantly less than in animals receiving [$^{18}$F]5a. At 60 minutes after [$^{18}$F]5a injection, the brain uptake was 0.054% ID/g versus 0.022% ID/g in animals receiving [$^{18}$F]5b ($p<0.03$ by a two-tailed t-test); at 120 minutes after [$^{18}$F]5a injection, the brain uptake was 0.050% ID/g versus 0.020% ID/g in animals receiving [$^{18}$F]5b ($p<0.003$ by a two-tailed t-test). The magnitude of the difference in brain uptake between the compounds is enough to account for the difference in tumor to brain uptake ratios at these time points.

It is likely that the difference in normal brain uptake of activity is due to the higher selectivity of [$^{18}$F]5b versus [$^{18}$F]5a for the A-type amino acid transport system, which is not active at the normal BBB [Betz, AL et al. (1978), *Science.* 202:225-227]. Some of the other amino acid transport systems, such as the L-type transport system, are active at the normal BBB [Uehara, H et al. (1997), *J. Cereb. Blood Flow Metab.* 17:1239-1253] and could potentially mediate uptake of these radiolabeled amino acids. The A-type amino acid transport system tolerates amino acid substrates with an N-methyl group while the other amino acid transport systems generally do not, [Palacin, M et al. (1998). *Pysiol. Rev.* 78:969-1054; Shotwell, MA et al. (1983), *Biochim. Biophys. Acta.* 737:267-284; Christensen, HN et al. (1983) *J. Med. Chem.* 26:1374-1378] and the uptake inhibition assays discussed earlier suggest that [$^{18}$F]5b is a more selective substrate for A-type transport than [$^{18}$F]5a. The lower uptake of activity observed with [$^{18}$F]5b relative to [$^{18}$F]5a in normal brain but not in tumor or pancreatic tissue is consistent with the increased selectivity of N-methyl amino acids for the A-type amino acid transport system. If [$^{18}$F]5a and [$^{18}$F]5b were entering normal brain by diffusion alone, the more lipophilic [$^{18}$F]5b would be expected to show higher brain uptake than [$^{18}$F]5a.

The high uptake of [$^{18}$F]5a and [$^{18}$F]5b in tumor tissue combined with low uptake in normal brain accounts for the high tumor to brain ratios observed with these compounds, but the low uptake across the normal BBB may also present difficulties in PET imaging studies of brain tumors. Disruptions of the BBB due to non-neoplastic processes may lead to increased uptake of radioactivity in lesions relative to normal brain tissue. Conversely, low-grade neoplasms may have normal BBBs that do not permit these radiotracers to reach the tumor cells. These potential problems must be addressed as the compounds undergo further evaluation. However, subtle alterations in BBB metabolism and transport may precede gross disruption of the BBB in low grade tumors, and tumors outside the CNS would not be liable to this effect In summary, both [$^{18}$F]FAMP (5a) and [$^{18}$F]NMeFAMP (5b) can be produced in high radiochemical yield (>78% EOB) and high radiochemical purity from stable precursors and are valuable agents for imaging brain tumors with PET. The synthetic strategy developed for [$^{18}$F]5a provides an efficient route for preparing radiolabeled primary amines with $^{18}$F in the β position. Uptake inhibition studies using 9L gliosarcoma cells demonstrated that both compounds are substrates for the A-type amino acid transport system, and these compounds represent the first report of $^{18}$F-labeled amino acids that undergo significant uptake via A-type transport. Biodistribution studies with both compounds showed rapid and persistent accumulation of radioactivity in rodent brain tumors with an excellent signal to background ratio. Injection of [$^{18}$F]5b led to ratios of 104:1 and 97:1 in tumor versus normal brain at 60 and 120 minutes, respectively, while injection of [$^{18}$F]5a led to ratios of 36:1 and 37:1 at the same time points. With the exception of the pancreas and kidneys, other tissues studied including muscle, lung, heart and liver showed relatively low uptake of radioactivity. Studies are currently underway to determine the toxicity, metabolic stability and radiation dosimetry associated with [$^{18}$F]5a and [$^{18}$F]5b administration and to determine the transport properties of the isolated R and S enantiomers of these compounds.

It will be understood that compounds of the invention can be labeled with an isotope of any atom or combination of atoms in the structure. While [$^{18}$F], [$^{123}$I], [$^{124}$I], and [$^{125}$I] have been is emphasized herein as being particularly useful for PET, SPECT, and tracer analysis, other uses are contemplated including those flowing from physiological or pharmacological properties of stable isotope homologs and will be apparent to those skilled in the art.

A high degree of tumor specific binding has been observed for compounds of the invention, in human patients as well as in experimental animals. The high specificity has inspired the use of At-substituted compounds of the invention for therapeutic use. At isotopes are emitters of alpha particles, where short range is useful for tumor radiotherapy.

The invention also provides for technetium (Tc) labeling via Tc adducts. Isotope of Tc, notably Tc$^{99m}$, have been used for tumor imaging. The present invention provides Tc-complexed adducts of compounds useful for tumor imaging. The adducts are Tc-coordination complexes joined to the cyclic and noncylcic amino acid by a 4-6 carbon chain which can be saturated or possess a double or triple bond. Where a double bond is present, either E (trans) or Z (cis) isomers can be synthesized, and either isomer can be employed. Synthesis

EXAMPLES

All reagents used were obtained from commercially available sources. Solvents used in reactions were purchased from Aldrich Chemicals while solvents for chromatography were obtained from VWR. Melting points are uncorrected and were determined in capillary tubes on an Electrochemical 9100 apparatus. $^1$H NMR spectra were recorded on a Varian spectrometer at 400 MHz unless otherwise indicated and referenced to the NMR solvent (chemical shifts in δ values, J in Hz). Mass spectra were determined on a VG 70-S double focusing mass spectrometer using high resolution electron ionization. Elemental analyses were performed by Atlantic Microlabs, Inc. and were within ±0.4% unless otherwise stated. The phrase "usual work up" refers to the use of anhydrous magnesium sulfate followed by concentration under reduced pressure. The compounds 3-benzyloxypropanone [Boger, DL et al. (1992), *J. Amer. Chem. Soc.* 114:9318-9327] and bis(4-methoxyphenyl)chloromethane [Dutta, AK et al. (1996), *J. Med. Chem.* 39:749-756] were prepared according to literature procedures. The target compounds 5a and 5b were prepared as racemic mixtures in both their fluorine-18 and fluorine-19 forms.

2-amino-2-cyano-3-fluoropropane (1). To a solution of 1 eq NH$_4$Cl (700 mg) and 1 eq KCN (853 mg) in 10 mL of H$_2$O was added fluoroacetone (1.0 g, 13.1 mmol) in 3 mL of H$_2$O. After overnight stirring at room temperature, the reaction mixture was basified with 10 mL of 1N NaOH and extracted with 5×20 mL of Et$_2$O. Usual work up afforded the aminonitrile 1 as a clear oil (510 mg, 38%) which was used without further purification: $^1$H NMR (CDCl$_3$), 300 MHz δ1.48 (3H, d, J=2.1), 4.17-4.33 (1H, m), 4.33-4.49 (1H, m).

2-[N-tert-butoxycarbonyl)amino]-3-fluoro-2-methylpropanoic acid (2). The crude aminonitrile 1 (510 mg, 5.00 mmol) was refluxed overnight in 20 mL of 6N HCl, and the solvent was removed under reduced pressure. The crude white solid was dissolved in 20 mL of 85:15 CH$_3$OH:Et$_3$N and treated with 2.6 eq of di-tert-butyl dicarbonate (2.8 g). After overnight stirring, the solvent was removed under reduced pressure, and the resulting paste was stirred in ice-cold 1:1 EtOAc:0.2N aqueous HCl for 5 minutes. The aqueous layer was further extracted with 2×50 mL of ice-cold EtOAc. The combined organic layers were washed with 2×50 mL of H$_2$O followed by usual work up. Purification by silica gel column chromatography (10% CH$_3$OH in CH$_2$Cl$_2$) provided 2 (767 mg, 69%) as a light yellow solid suitable for use in the next step. Analytically pure samples were obtained using the same procedure followed by further purification by silica gel column chromatography (1:3 EtOAc:hexane followed by 1:1 EtOAc:hexane) to provide the N-Boc acid 2 as a white solid: mp 122-123 EC (EtOAc/hexane); $^1$H NMR (CDCl$_3$) δ 1.45 (9H, s), 1.56 (3H, d, J=1.6), 4.74 (2H, d, J=46.8), 5.30 (1H, broad s). Anal. (C$_9$H$_{16}$FNO$_4$)C,H,N.

2[N-tert-butoxycarbonyl)amino]-3-fluoro-2-methylpropanoic acid tert-butyl ester (3). The N-Boc acid 2 (767 mg, 3.46 mmol) in 10 mL of dry CH$_2$Cl$_2$ was stirred overnight with 3 eq of tert-butyl-2,2,2-tricholoracetimdate (2.27 g). After concentration under reduced pressure, the crude product was purified by silica gel column chromatography (5% EtOAc in hexane) to provide 3 (510 mg, 53%) as a white solid: mp 41-42 EC (EtOAc/hexane); $^1$H NMR (CDCl$_3$) δ 1.44 (9H, s), 1.47 (3H, d, J=2.4), 1.48 (9H, s), 4.57-4.85 (2H, m), 5.34 (1H, broad s). Anal. (C$_{13}$H$_{24}$FNO$_4$)C,H,N.

2-[N-(tert-butoxycarbonyl)methylamino]-3-fluoro-2-methylpropanoic acid tert-butyl ester (4). To a solution of 3 (200 mg, 0.72 mmol) in dry DMF under an argon atmosphere was added 8 eq of CH$_3$I (0.36 mL) followed by 2 eq of 95% NaH (37 mg). The reaction mixture was stirred overnight at room temperature. The reaction mix was added to 15 mL of H$_2$O and extracted with 3×15 mL of Et$_2$O. The combined organic layers were washed with 3×20 mL H$_2$O followed by the usual work up. Purification of the crude product via silica gel column chromatography (7.5% EtOAc in hexane) afforded the methylated species 4 (181 mg, 86%) as a colorless oil: $^1$H NMR (CDCl$_3$) δ 1.44 (9H, s), 1.46 (9H, s), 1.51 (3H, s), 2.94 (3H, s), 4.51-5.04 (2H, m). Anal. (C$_{14}$H$_{26}$FNO$_4$)C,H,N.

2-amino-3-fluoro-2-methylpropanoic acid (5a), hydrochloride salt. The N-Boc amino acid 2 (30 mg, 0.14 mmol) was suspended in 0.3 mL of 4N HCl and heated to 50° C. for 90 minutes. The resulting homogeneous solution was evaporated under reduced pressure to provide the crude HCl salt of the amino acid. The solid was washed with 2×10 mL of Et$_2$O to provide 5a (18 mg, 84%) as a white solid: decomp 204-206 EC; $^1$HNMR (D$_2$O) δ 1.52 (3H, s), 4.55-4.91 (2H, m). Anal. (C$_4$H$_9$ClFNO$_2$)C,H,N.

3-fluoro-2-methyl-2-methylamino)propanoic acid (5b), hydrochloride salt The N-Boc tert-butyl ester 4 (30 mg, 0.10 mmol) was stirred in 0.6 mL of 6N HCl and heated to 70 EC for 3 hours. The resulting solution was evaporated under reduced pressure, and the solid was washed with 2×10 mL of Et$_2$O to provide 5b (16 mg, 91%) as a white solid: decomp 178-181° C.; $^1$H NMR (D$_2$O) δ 1.47-1.48 (3H, m), 2.73 (3H, s), 4.64-4.90 (2H, m). Anal. (C$_5$H$_{11}$ClFNO$_2$)C,H,N.

1-methyl-1-(benzyloxymethyl)hydantoin (6). To a solution of 3-benzyloxypropanone (5.7 g, 34.7 mmol) in 180 mL of 1:1 EtOH:H$_2$O was added 10 eq of ammonium carbonate (33 g) followed by 4 eq of ammonium chloride (7.42 g). After stirring at room temperature for 30 minutes, a 4.5 eq portion of potassium cyanide (10.2 g) was added, and the reaction mix was stirred for 48 hours at room temperature. The solvent was evaporated under reduced pressure, and the resulting solid was washed with 3×30 mL of water to afford the hydantoin 6 (6.4 g, 79% yield) as a yellowish solid suitable for use in the next step. Analytically pure samples were obtained via chromatography on silica gel (EtOAc): mp 94.5-96° C. (EtOAc); $^1$H NMR (CDCl$_3$) δ 1.43 (3H, s), 3.47 (1H, d, J=9.6), 3.62 (1H, d, J=9.6), 4.50-4.60 (2H, m), 5.37 (1H, broad s), 7.27-7.38 (5H, m) 7.45 (1H, broad s). Anal. (C$_{12}$H$_{14}$N$_2$O$_3$)C, H, N.

3-benzyloxy-2-[N-(tert-butoxycarbonyl)amino]-2-methylpropanoic acid (7). A suspension of the hydantoin 6 (2.0 g, 8.5 mmol) in 55 mL of 5 M NaOH was heated at 180 EC overnight in a sealed steel vessel. After cooling, the reaction mix was brought to pH 7 using concentrated HCl, and the solvent was evaporated under reduced pressure. The white solid was extracted with 4×20 mL of hot EtOH, and the combined extracts were concentrated under reduced pressure. The resulting residue was dissolved in 50 mL of 9:1 CH$_3$OH:Et$_3$N and treated with 2 eq of di-tert-butyl dicarbonate (3.72 g) overnight at room temperature. The reaction mixture was concentrated under reduced pressure and purified by silica gel column chromatography (5% CH$_3$OH in CH$_2$Cl$_2$) to afford 7 as an off-white solid (1.76 g, 67%): mp 112.5-114.5° C. (CH$_3$OH/CH$_2$Cl$_2$); $^1$H NMR (CDCl$_3$) δ 1.45 (9H, s), 1.46 (3H, s), 3.72 (1H, d J=9.2), 3.81 (1H, d, J=9.6), 4.59 (2H, d, J=1.6), 5.44 (1H, broad s), 7.30-7.38 (5H, m). Anal. (C$_{16}$H$_{23}$NO$_5$)C,H,N.

3-benzyloxy-2-[N-tert-butoxycarbonyl)amino]-2-methylpropanoic acid tert-butyl ester (8). To a solution of the N-Boc carboxylic acid 7 (1.6 g, 5.17 mmol) in 15 mL of CH$_2$Cl$_2$ at room temperature was added a 3 eq portion of tert-butyl-2,2,2-trichloroacetamidate (3.4 g). After overnight stirring at room temperature, the solvent was evaporated under reduced pressure. Purification via silica gel column chromatography (15% EtOAc in hexane) afforded 8 as a colorless oil (1.71 g, 90%): $^1$H NMR (CDCl$_3$) δ 1.44 (9H, s), 1.45 (9H, s), 1.48 (3H, s), 3.66 (1H, d, J=8.8), 3.79-3.82 (1H, broad d), 4.48-4.58 (2H, m), 5.51 (1H, broad s), 7.28-7.35 (5H, m). Anal. (C$_{20}$H$_{31}$NO$_5$)C,H,N.

2-[N-(tert-butoxycarbonyl)amino]-3-hydroxy-2-methylpropanoic acid tert-butyl ester (9). A suspension of the benzyl ether 8 (540 mg, 1.48 mmol) and 10% Pd—C (130 mg) in 20 mL of CH$_3$OH was stirred under an H$_2$ atmosphere overnight. The reaction mixture was filtered over Celite?, and the filtrate was concentrated under reduced pressure. Purification via silica gel column chromatography (30% EtOAc in hexane) provided a quantitative yield of 9 (407 mg, 100%) as a colorless solid: mp 44-45° C. EtOAc/hexane; $^1$H NMR (CDCl$_3$) δ 0.437 (3H, s), 1.442 (9H, s), 1.48 (9H, s), 3.72 (1H, d, J=11.2), 4.00 (1H, d, J=11.2), 5.32 (1H, broad s). Anal. (C$_{13}$H$_{25}$NO$_5$)C,H,N.

3-benzyloxy-2-[N(tert-butoxycarbonyl)methylamino]-2-methylpropanoic acid tert-butyl ester (10). The same procedure used to obtain 4 was employed using 745 mg of 8 (2.04 mmol). The crude product was purified via silica gel column chromatography (10% EtOAc in hexane) to provide 10 (770 mg, 99%) as a colorless oil: $^1$H NMR (CDCl$_3$) δ 1.43 (18H, s), 1.50 (3H, s), 2.96 (3H, s), 3.67 (1H, d, J=10), 4.04 (1H, broad s), 4.52 (2H, s), 7.24-7.34 (5H, m). Anal. (C$_{21}$H$_{33}$NO$_5$)C,H,N.

2-[N-(tert-butoxycarbonyl)methylamino]-3-hydroxy-2-methylpropanoic acid tert-butyl ester (11). The same hydrogenolysis conditions used to convert 8 to 9 were applied to a 350 mg portion of 10 (0.92 mmol) to afford 11 (266 mg, 100%) as a colorless oil: $^1$H NMR (CDCl$_3$) δ 1.45-1.46 (21H, m), 2.88 (3H, s), 3.50 (1H, d, J=14.8 Hz), 4.02 (1H, J=15.6 Hz). Anal. (C$_{14}$H$_{27}$NO$_5$)C,H,N.

3-hydroxy-2-(N-[bis(4-methoxyphenyl)methyl]amino)2-methylpropanoic acid tert-butyl ester (12a). To a solution of the alcohol 9 (100 mg, 0.36 mmol) in 2 mL of diethyl ether was added 1 eq of p-toluenesulfonic acid monohydrate (69 mg) dissolved in 6 mL of EtOH. The reaction mixture was concentrated under reduced pressure at 40° C., and the residue was dissolved in 6 mL of EtOH and concentrated again. This process was repeated 4 times, at which time no starting material was present on TLC analysis. The resulting white solid was suspended in 3 mL of CH$_2$Cl$_2$, and treated with 4.5 eq of triethylamine (0.23 mL) followed by 1 eq of bis(4-methoxyphenyl)chloromethane (95 mg). The reaction mixture was stirred for 1 hour at room temperature. The solution was then partitioned between 10 mL of EtOAc and 10 mL of H$_2$O. The aqueous layer was extracted with 10 mL of EtOAc followed by the usual work up of the combined organic layers. Purification by silica gel column chromatography (20% EtOAc in hexane) provided the amino ester 12a as a colorless oil (107 mg, 73% from 9): $^1$H NMR (CDCl$_3$) δ 1.17 (3H, s), 1.46 (9H, s), 3.35 (1H, d, J=11.2), 3.44 (1H, d, J=11.2), 3.76 (3H, s), 3.77 (3H, s), 4.82 (1H, s), 6.80-6.84 (4H, m), 7.27-7.31 (4H, m). Anal. (C$_{23}$H$_{31}$NO$_5$)C,H,N.

3-hydroxy-2-methyl-2-methylamino)propanoic acid tert-butyl ester (12b). A 255 mg portion of alcohol 11 (0.88 mmol) was treated with 1 eq p-toluenesulfonic acid (167 mg) as described in the preparation of 12a. The resulting solid was added to 15 mL of 10% Na$_2$CO$_3$ and extracted with 3×15 mL of EtOAc. The combined organic layers were subject to the usual work up. Purification via silica gel column chromatography (10% CH$_3$OH in CH$_2$Cl$_2$) afforded 12b (115 mg, 69%) as a colorless oil: $^1$H NMR (CDCl$_3$) δ 1.24 (3H, s), 1.48 (9H, s), 2.32 (3H, s), 3.52 (1H, d, J=10.8), 3.64 (1H, d, J=10.8). HRMS Calcd for C$_9$H$_{19}$NO$_3$: 189.13649. Found 189.13627. Anal. (C$_9$H$_{19}$NO$_3$) Calcd C: 57.12, H: 10.12, N: 7.40. Found C: 55.87, H: 10.05, N: 7.18.

3-[bis(4-methoxyphenyl)methyl]-4-methyl-1,2,3-oxathiazolidine-4-carboxylic acid tert-butyl ester 2-oxide (13a). A solution of the amino alcohol 12a (105 mg, 0.26 mmol) and 2.2 eq of triethylamine (80 μL) in 8 mL of toluene under an argon atmosphere was cooled in an ice bath followed by the dropwise addition of 1.1 eq of thionyl chloride (34 mg) in 1 mL of toluene. After 15 minutes the ice bath was removed, and the reaction was continued for 10 minutes. The reaction mix was partitioned between 10 mL of EtOAc and 10 mL of H$_2$O. The aqueous layer was further extracted with 3×10 mL of EtOAc. The organic layers were combined and washed with 20 mL of brine followed by usual work up. Silica gel column chromatography (25% EtOAc in hexane) afforded a 1.6:1 mixture of cyclic sulfairdite diastereomers 13a as a colorless oil (97 mg, 83%): $^1$H NMR (CDCl$_3$) for major diastereomer: δ 1.32 (9H, s), 1.37 (3H, s), 3.78 (3H, s), 3.79 (3H, s), 4.23 (1H, d, J=8.4), 5.34 (1H, d, J=8.8), 5.91 (1H, s), 6.83-6.86 (4H, m), 7.17-7.20 (2H, m), 7.38-7.41 (2H, m). $^1$H NMR (CDCl$_2$) for minor diastereomer: δ 1.21 (3H, s), 1.53 (9H, s), 3.77 (3H, s), 3.81 (3H, s), 4.67 (2H, s), 5.74 (1H, s), 6.82-6.91 (4H, m), 7.33-7.36 (2H, m), 7.51-7.54 (2H, m). Anal. for mixture of diastereomers: (C$_{23}$H$_{29}$NO$_6$S)C,H,N.

3,4dimethyl-1,2,3-oxathiazolidine-4-carboxylic acid tert-butyl ester 2-oxide (13b). A solution containing a 103 mg portion of 12b (0.55 mmol) and a 2.2 eq portion of triethylamine (0.17 mL) in 2 mL CH$_2$Cl$_2$ was added dropwise to a solution of 1.1 eq thionyl chloride (72 mg) in 2 mL of dry CH$_2$Cl$_2$ under argon at −78° C. The reaction mix was allowed to warm to room temperature overnight. The reaction mix was partitioned between 10 mL of EtOAc and 10 mL of H$_2$O. The aqueous layer was further extracted with 2×10 mL of EtOAc. The organic layers were combined and washed with 20 mL of brine followed by usual work up. Purification by silica gel column chromatography (15% EtOAC in hexane) provided a 1.8:1 mixture of diastereomers 13b (76 mg, 58%) as a colorless oil. The mixture of diastereomers was used immediately in the next step as the compounds decomposed over time. The diastereomers could be separated in small amounts using the same chromatography conditions: $^1$H NMR (CDCl$_3$) for major diastereomer: δ 1.47 (9H, s), 1.56 (3H, s), 2.86 (3H, s), 4.55 (1H, d, J=9.2), 4.73 (1H, d, J=8.8). Anal. (C$_9$H$_{17}$NO$_4$S). Calcd C: 45.94, H: 7.28, N: 5.95. Found C: 45.10, H: 7.59, N: 5.64. $^1$H NMR (CDCl$_3$) for minor diastereomer δ 1.44 (3H, s), 1.49 (9H, s), 2.91 (3H, s), 4.03 (1H, d, J=8.0), 5.22 (1H, d, J=8.4). Anal. (C$_9$H$_{17}$NO$_4$S). Calcd C: 45.94, H: 7.28, N: 5.95. Found C: 46.48, H: 7.41, N: 5.78.

3-[bis(4-methoxyphenyl)methyl]-4methyl-1,2,3-oxathiazolidine-4-carboxylic acid tert-butyl ester 2,2-dioxide (14a). A solution of the diastereomeric sulfamidites 13a (97 mg, 0.22 mmol) in 4 mL of CH$_3$CN was cooled in an ice bath and treated successively with 1.1 eq of NaIO$_4$ (51 mg), a catalytic amount of RuO$_2$.H$_2$O (~1 mg) and 2.4 mL of H$_2$O. After 5 minutes of stirring the ice bath was removed, and the reaction was continued for 20 minutes. The reaction mixture was diluted in 10 mL of EtOAc and washed with 10 mL of saturated NaHCO$_3$ solution. The aqueous layer was extracted with 2×10 mL of EtOAc, and the combined organic layers were washed with 10 mL brine followed by usual work up. The crude product was purified by silica gel column chromatography (30% EtOAc in hexane) to provide the cyclic sulfamidate 14a as a light yellow solid (90 mg, 89%): mp 143.5-145 EC (EtOAc.hexane); $^1$H NMR (CDCl$_3$) δ 1.29 (3H, s), 1.51 (9H, s), 3.77 (3H, s), 3.80 (3H, s), 4.16 (1H, d, J=8.8), 4.73 (1H, d, J=8.8), 5.98 (1H, s), 6.82-6.89 (4H, m), 7.38-7.44 (4H). Anal. ($C_{23}H_{29}NO_7S$)C,H,N.

3,4-dimethyl-1,2,3-oxathiazolidine-4-carboxylic acid tert-butyl ester 2,2-dioxide (14b). The same reaction conditions used to obtain 14a were applied to 42 mg of 13b (0.18 mmol), providing 14b (42 mg, 94%) as a white solid: mp 54-55° C. (EtOAc/hexane); $^1$H NMR (CDCl$_3$) δ1.50 (9H, s), 1.52 (3H, s), 2.93 (3H, s), 4.22 (1H, d, J=8.8), 4.88 (1H, d, J=8.8). Anal ($C_9H_{17}NO_5S$)C,H,N.

Preparation of 5a (FAMP) via 14a. To a solution of the cyclic sulfamidate 14a (130 mg, 0.28 mmol) in CH$_3$CN (4 mL) was added 3 eq of tetrabutylammonium fluoride (1.0 M in THF), and the resulting solution was stirred overnight at room temperature. The reaction mix was concentrated under reduced pressure, and the residue was treated with 5 mL of 3N HCl at 85° C. for 1 hour. After cooling, the aqueous solution was washed with 5 mL of ether and then brought to pH 7 with 6N NaOH. The solvent was removed under reduced pressure, and the resulting white solid was dissolved in 9:1 CH$_3$OH: Et$_3$N. To this solution was added a 2 eq portion of (Boc)$_2$O (122 mg), and the reaction mixture was stirred overnight at room temperature. The work up and purification were performed as previously described to provide the product 5a (25 mg, 40%) which had the same $^1$H NMR specttum as the product obtained via the aminonitrile route.

Radiosynthesis of [$^{18}$F]5a (FAMP) and [$^{18}$F]5b (N-Me-FAMP). The same conditions were used to prepare [$^{18}$F]5a from 14a and [$^{18}$F]5b from 14b. To a Wheaton vial containing 150-200 mCi of no-carrier-added [$^{18}$F]HF (20 μA, 10-15 minute bombardment theoretical specific activity of 1.7 Ci/mmole) in 350 μL of [$^{18}$O]H$_2$O was added a 1 mL solution of 10 mg K$_{222}$ Kryptofix and 1 mg of K$_2$CO$_3$ in CH$_3$CN. The solvent was removed at 115 EC with argon gas flow, and an additional 1 mL of CH$_3$CN was added followed by evaporation with argon flow. This drying was repeated a total of 3 times to remove residual H$_2$O. A 1-2 mg portion of the cyclic sulfamidate precursor 14a or 14b in 1 mL of dry CH3CN was added to the vial, and the reaction mix was heated at 85° C. for 20 minutes. The solvent was removed at 115° C. with argon gas flow, and the intermediate product was treated with 0.5 mL of 6N HCl at 85° C. for 10 minutes. The solution of radiolabeled amino acid was diluted in 1-2 mL of H$_2$O and eluted in H$_2$O through a 7×120 mm column of ion-retardation resin (Bio Rad AG11A8 50-100 mesh) in series with 2 Alumina N SepPaks® and 1 C-18 SepPak®. The eluting fractions containing radioactivity were used directly in rodent studies. The identity of the radiolabeled product was confirmed by comparing the R$_f$ of the radioactive product visualized with radiometric TLC with the R$_f$ of the authentic $^{19}$F compound visualized with ninhydrin stain (R$_f$=0.6, Alltech 0.25 mm RP Chiralplates, 20:5:5 CH$_3$CN:H$_2$O:MeOH). In all radiosyntheses, the only peak present on radiometric TLC analysis corresponded to 5a or 5b, and the radiochemical purity of the product exceeded 99%. The isolated radiochemical yields were determined using a dose-calibrator (Capintec CRC-712M).

Amino acid uptake inhibition assays. The 9L gliosarcoma cells were initially grown as monolayers in T-flasks containing Dulbecco's Modified Eagle's Medium (DMEM) under humidified incubator conditions (37° C., 5% CO$_2$/95% air). The growth media was supplemented with 10% fetal calf serum and antibiotics (10,000 units/ml penicillin and 10 mg/ml streptomycin). The growth media was replaced three times per week, and the cells were passaged so the cells would reach confluency in a week's time.

When the monolayers were confluent, cells were prepared for experimentation in the following manner. Growth media was removed from the T-flask, and the monolayer cells were exposed to 1× trypsin:EDTA for ~1 minute to weaken the protein attachments between the cells and the flask. The flask was then slapped, causing the cells to release. Supplemented media was added to inhibit the proteolytic action of the trypsin, and the cells were aspirated through an 18 Ga needle until they were monodisperse. A sample of the cells was counted under a microscope using a hemocytometer, and the live/dead fraction estimated through trypan blue staining (>98% viability). The remainder of the cells was placed into a centrifuge tube, centrifuged at 75 G for 5 minutes, and the supernatant was removed. The cells were then resuspended in amino-acid/serum-free DMEM salts.

In this study, approximately 4.55×10$^5$ cells were exposed to either [$^{18}$F]5a or [$^{18}$F]5h (5 μCi) in 3 ml of amino acid free media±transporter inhibitors (10 mM) for 30 minutes under incubator conditions in 12×75 mm glass vials. Each assay condition was performed in duplicate. After incubation, cells were twice centrifuged (75 G for 5 minutes) and rinsed with ice-cold amino-acid/serum-free DMEM salts to remove residual activity in the supernatant. The vials were placed in a Packard Cobra II Auto-Gamma counter, the raw counts decay corrected, and the activity per cell number determined. The data from these studies (expressed as percent uptake relative to control) were graphed using Excel, with statistical comparisons between the groups analyzed using a 1-way ANOVA (GraphPad Prism software package).

Tumor induction and animal preparation. All animal experiments were carried out under humane conditions and were approved by the Institutional Animal Use and Care Committee (IUCAC) at Emory University. Rat 9L gliosarcoma cells were implanted into the brains of male Fischer rats as described previously [Shoup, TM et al. (1999), *J. Nucl. Med.* 40:331-338]. Briefly, anesthetized rats placed in a stereotactic head holder were injected with a suspension of 4×10$^4$ rat 9L gliosarcoma cells (1×10$^7$ per mL) in a location 3 mm right of midline and 1 mm anterior to the bregma at a depth of 5 mm deep to the outer table. The injection was performed over the course of 2 minutes, and the needle was withdrawn over the course of 1 minute to minimize the backflow of tumor cells. The burr hole and scalp incision were closed, and the animals were returned to their original colony after recovering from the procedure. Intracranial tumors developed that produced weight loss, apathy and hunched posture in the tumor-bearing rats, and the animals were used at 17-19 days after implantation. Of the 30 animals implanted with tumor cells, 25 developed tumors visible to the naked eye upon dissection and were used in the study.

Rodent biodistribution studies. The same procedures were used to evaluate [$^{18}$F]5a and [$^{18}$F]5b separately in rodents. The tissue distribution of radioactivity was determined in 16 normal male Fischer 344 rats (200-250 g) after intravenous injection of 85 μCi of [$^{18}$F]5a or [$^{18}$F]5b in 0.3 mL of sterile water. The animals were allowed food and water ad libitum before the experiment. Following anesthesia induced with an intramuscular injection of 0.1 mL/100 g of a 1:1 ketamine (500 mg/mL):xylazine (20 mg/mL) solution, the radiolabeled amino acid was injected into the rats via tail vein catheters. Groups of four rats were killed at 5 minutes, 30 minutes, 60 minutes and 120 minutes after injection of the dose. The animals were dissected, and selected tissues were weighed and counted along with dose standards in a Packard Cobra II AutoGammna Counter. The raw counts were decay corrected, and the counts were normalized as the percent of total injected dose per gram of tissue (% ID/g). A comparison of the uptake of activity in the tissues at each time point was analyzed using a 1-way ANOVA (GraphPad Prism software package).

The tissue distribution of radioactivity was also determined in tumor-bearing Fischer 344 rats following intravenous injection of ~35 μCi of [$^{18}$F]5a or [$^{18}$F]5b in 0.3 mL of sterile water. The procedure was similar to that already described for normal rats with the following modifications. The tail vein injections were performed in awake animals using a RTV-190 rodent restraint device (Braintree Scientific) to avoid mortality accompanying anesthesia in the presence of an intracranial mass. The animals were killed at 5 minutes, 60 minutes or 120 minutes post-injection. The same tissues were assayed as in normal rats with the addition of the tumor tissue, and the corresponding region of brain contralateral to the tumor was excised and used for comparison. The uptake in the tumor and contralateral brain at each time point was compared via a two-tailed t-test for paired observations (GraphPad Prism software package).

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the invention is to be limited only to the claims except as precluded by the prior art. Moreover, the invention as disclosed herein, may be suitably practiced in the absence of the specific elements which are disclosed herein.

All references cited in the present application are incorporated in their entirety herein by reference to the extent not inconsistent herewith.

Scheme 1. Synthesis of florine-19 amino acids FMAP (5a) and N-MeFAMP (5b).

(a) KCN, NH$_4$Cl, H$_2$O; (b) HCl then (Boc)$_2$O;
(c) aqueous HCl; (d) Cl$_3$CC(=NH)OtBu, CH$_2$Cl$_2$; (e) NaH, DMF, CH$_3$I.

Scheme 2. Synthesis of 3-benzyloxy-2-[N-(tert-butoxycarbonyl)amino]-2-methylpropanoic acid tert-butyl ester (8).

(a) (NH$_4$)$_2$CO$_3$, KCN, NH$_4$Cl, 1:1 EtOH:H$_2$O;
(b) 5 N NaOH, 180° C. then (Boc)$_2$O, 9:1 CH$_3$OH:Et$_3$N; (c) Cl$_3$CC(=NH)OtBu, CH$_2$Cl$_2$.

Scheme 3. Synthesis of N-substituted aminoalcohols 12a and 12b.

(a) 10% Pd/C, H$_2$, CH$_3$OH;
(b) pTsOH—H$_2$O, EtOH, 40° C.;
(c) DMB—Cl, Et$_3$N, CH$_2$Cl$_2$;
(d) NaH, DMF, CH$_3$I.

pTsOH = p-toluenesulfonic acid
DMB = bis(4-methoxyphenyl)methyl

Scheme 4. Synthesis of cyclic sulfamidates 14a and 14b and radiosynthesis of [$^{18}$F]FAMP (5a) and [$^{18}$F]N-MeFAMP (5b).

(a) SOCl$_2$, Et$_3$N, toluene or CH$_2$Cl$_2$;
(b) NaIO$_4$, cat. RuO$_2$, H$_2$O, CH$_3$CN;
(c) [$^{18}$F]HF, K$_{2,2,2}$, K$_2$CO$_3$, CH$_3$CN, 85° C. then 6N HCl, 85° C.

TABLE I

Tissue distribution of radioactivity in normal Fischer rats after injection of [$^{18}$F]FAMP (5a)

| Tissue | 5 min | 30 min | 60 min | 120 min |
| --- | --- | --- | --- | --- |
| Blood | 0.53 ± 0.03 | 0.25 ± 0.014 | 0.22 ± 0.02 | 0.15 ± 0.005 |
| Heart | 0.29 ± 0.012 | 0.29 ± 0.04 | 0.28 ± 0.013 | 0.23 ± 0.03 |
| Lung | 0.55 ± 0.006 | 0.54 ± 0.12 | 0.44 ± 0.05 | 0.37 ± 0.10 |
| Liver | 0.65 ± 0.05 | 0.56 ± 0.04 | 0.50 ± 0.013 | 0.48 ± 0.03 |
| Spleen | 0.83 ± 0.05 | 0.54 ± 0.03 | 0.50 ± 0.04 | 0.33 ± 0.02 |
| Pancreas | 3.46 ± 0.19 | 2.93 ± 0.20 | 2.95 ± 0.27 | 2.48 ± 0.03 |
| Kidney | 6.36 ± 0.36 | 5.59 ± 0.28 | 4.74 ± 0.15 | 2.97 ± 0.17 |
| Bone | 0.27 ± 0.005 | 0.22 ± 0.02 | 0.19 ± 0.03 | 0.13 ± 0.012 |
| Muscle | 0.22 ± 0.013 | 0.22 ± 0.009 | 0.26 ± 0.04 | 0.19 ± 0.003 |
| Testis | 0.17 ± 0.010 | 0.10 ± 0.006 | 0.12 ± 0.006 | 0.10 ± 0.004 |
| Brain | 0.04 ± 0.003 | 0.05 ± 0.004 | 0.06 ± 0.004 | 0.05 ± 0.001 |

Values are reported as mean percent dose per gram ± standard error.
n = 4 at each time point.

TABLE II

Tissue distribution of radioactivity in normal Fischer rats after injection of [$^{18}$F]N-MeFAMP (5b)

| Tissue | 5 min | 30 min | 60 min | 120 min |
| --- | --- | --- | --- | --- |
| Blood | 0.61 ± 0.02 | 0.30 ± 0.003 | 0.18 ± 0.02 | 0.10 ± 0.007 |
| Heart | 0.22 ± 0.01 | 0.23 ± 0.03 | 0.20 ± 0.02 | 0.17 ± 0.02 |
| Lung | 0.53 ± 0.03 | 0.50 ± 0.07 | 0.38 ± 0.07 | 0.30 ± 0.08 |
| Liver | 0.79 ± 0.06 | 0.72 ± 0.09 | 0.78 ± 0.10 | 0.58 ± 0.11 |
| Spleen | 0.44 ± 0.06 | 0.75 ± 0.06 | 0.68 ± 0.02 | 0.47 ± 0.04 |
| Pancreas | 2.73 ± 0.28 | 3.00 ± 0.23 | 3.24 ± 0.30 | 2.88 ± 0.40 |
| Kidney | 8.12 ± 0.62 | 4.60 ± 0.70 | 2.73 ± 0.35 | 1.36 ± 0.27 |
| Bone | 0.34 ± 0.04 | 0.32 ± 0.04 | 0.29 ± 0.04 | 0.20 ± 0.02 |
| Muscle | 0.16 ± 0.008 | 0.16 ± 0.003 | 0.15 ± 0.007 | 0.13 ± 0.007 |
| Testis | 0.17 ± 0.004 | 0.11 ± 0.005 | 0.08 ± 0.005 | 0.06 ± 0.005 |
| Brain | 0.04 ± 0.005 | 0.04 ± 0.004 | 0.03 ± 0.003 | 0.03 ± 0.001 |

Values are reported as mean percent dose per gram ± standard error.
n = 4 at each time point.

TABLE III

Tissue distribution of radioactivity in tumor-bearing Fischer rats after injection of [$^{18}$F]FAMP (5a)

| Tissue | 5 min | 60 min | 120 min |
| --- | --- | --- | --- |
| Blood | 0.72 ± 0.05 | 0.26 ± 0.03 | 0.16 ± 0.01 |
| Heart | 0.40 ± 0.04 | 0.33 ± 0.06 | 0.22 ± 0.02 |
| Lung | 0.84 ± 0.03 | 0.38 ± 0.04 | 0.24 ± 0.03 |
| Liver | 0.77 ± 0.22 | 0.66 ± 0.16 | 0.25 ± 0.02 |
| Spleen | 0.72 ± 0.06 | 0.55 ± 0.08 | 0.32 ± 0.02 |
| Pancreas | 5.31 ± 0.68 | 2.86 ± 0.34 | 1.42 ± 0.17 |
| Kidney | 8.66 ± 1.27 | 6.20 ± 1.45 | 3.64 ± 0.26 |
| Bone | 0.38 ± 0.04 | 0.25 ± 0.05 | 0.16 ± 0.01 |
| Muscle | 0.39 ± 0.02 | 0.31 ± 0.03 | 0.21 ± 0.01 |
| Testis | 0.22 ± 0.02 | 0.14 ± 0.02 | 0.11 ± 0.003 |
| Brain | 0.035 ± 0.002* | 0.054 ± 0.01** | 0.050 ± 0.004† |
| Tumor | 0.91 ± 0.05* | 1.96 ± 0.10** | 1.87 ± 0.2† |
| Tumor:Brain Ratio | 26:1 | 36:1 | 37:1 |

Values are reported as mean percent dose per gram ± standard error.
n = 4 at 5 min,
n = 5 at 60 min,
n = 4 at 120 min;
p values determined using two-tailed t-test for pairwise comparisons.
*= p < 0.001,
**= p < 0.001,
†= p < 0.003

TABLE IV

Tissue distribution of radioactivity in tumor-bearing Fischer rats after injection of [$^{18}$F]N-MeFAMP (5b)

| Tissue | 5 min | 60 min | 120 min |
| --- | --- | --- | --- |
| Blood | 0.69 ± 0.04 | 0.17 ± 0.02 | 0.10 ± 0.007 |
| Heart | 0.34 ± 0.02 | 0.25 ± 0.03 | 0.19 ± 0.02 |
| Lung | 0.61 ± 0.04 | 0.26 ± 0.03 | 0.19 ± 0.011 |
| Liver | 0.94 ± 0.12 | 0.85 ± 0.17 | 0.41 ± 0.06 |
| Spleen | 0.47 ± 0.04 | 0.45 ± 0.06 | 0.40 ± 0.02 |
| Pancreas | 2.95 ± 0.58 | 2.42 ± 0.27 | 1.74 ± 0.24 |
| Kidney | 9.33 ± 0.36 | 2.79 ± 0.31 | 1.59 ± 0.19 |
| Bone | 0.33 ± 0.04 | 0.23 ± 0.04 | 0.19 ± 0.02 |
| Muscle | 0.22 ± 0.011 | 0.19 ± 0.02 | 0.16 ± 0.012 |
| Testis | 0.19 ± 0.008 | 0.08 ± 0.008 | 0.08 ± 0.005 |
| Brain | 0.032 ± 0.002* | 0.022 ± 0.006** | 0.020 ± 0.005† |
| Tumor | 1.29 ± 0.28* | 2.28 ± 0.16** | 1.94 ± 0.12† |
| Tumor:Brain Ratio | 40:1 | 104:1 | 97:1 |

Values are reported as mean percent dose per gram ± standard error.
n = 4 at each time point;
p values determined using two-tailed t-test for pairwise comparisons.
*= p < 0.02,
**= p < 0.001,
†= p < 0.001

We claim:
1. An amino acid analog having the general structure

$$R_1\text{---}(CH_2)_a\text{---}\underset{\underset{C_yH_z\text{---}NHR_4}{|}}{\overset{\overset{COOH}{|}}{C}}\text{---}R_2$$

where $R_1$ is X, $$X\text{---}HC\text{=}CH\text{---},$$

or $R_3$
$R_2$ is H, or $R_3$ if $R_1$ is $R_3$, $$R_3 \text{ is } X\text{---}(CH)_j\text{---}C_mH_n\text{---}CH_q\overset{(CH_2)_x}{\underset{\diagdown}{\diagup}}$$

such that $$R_3\left\langle\left[\underset{\underset{C_yH_z\diagup\quad\diagdown NHR_4}{}}{\overset{CH_2\diagdown\quad\diagup COOH}{C}}\right]\right.$$

is formed,
$R_4$ is $CH_3$, $\text{---}(C_kH_{2k+1})$, $\text{---}(C_kH_{2k-1})$ or $\text{---}(C_kH_{2k-3})$ where k=2-5
And where
  a is 1 to 5,
  x is 0 or 1,
  y is 1 or 2,
  z is 1, 2, 3 or 4 and z>y if y is 2,
  q is 1 or 0 if n is 1 and j is 0,
  n is 1 or 2, but 0 if m is 0,
  m is 0 or 1
  j is 0, 1, 2 or 3 and
  X is $^{18}$F, $^{123}$I, $^{124}$I, $^{125}$I, $^{131}$I, $^{75}$Br, $^{76}$Br, $^{77}$Br, $^{82}$Br, or At.
2. The compound of claim 1, wherein $R_1$ and $R_2$ are $R_3$.
3. The compound of claim 1, wherein x is 0
y is 1
z is 2
q is 1
m is 0 and j is 0.
4. The compound of claim 3, wherein X is $^{18}$F or $^{123}$I.
5. The compound of claim 3, wherein X is $^{18}$F.
6. The compound of claim 1, wherein $R_1$ and $R_2$ are $R_3$,
x is 0 or 1
y is 2
z is 4
q is 1
m and j are 0 and X is $^{18}$F or $^{123}$I.
7. The compound of claim 6, wherein x is 1 and X is $^{18}$F.
8. The compound of claim 6, wherein x is 0 and X is $^{123}$I.
9. The compound of claim 6, wherein x is 1 and X is $^{123}$I.
10. The compound of claim 1, wherein R1 and R2 are R3,
x is 0
y is 1
z is 2
q is 0
m is 1
n is 1
j is 0 and X is $^{18}$F or $^{123}$I.
11. The compound of claim 10, wherein X is $^{18}$F.
12. A compound according to claim 1 wherein $R_1$ and $R_2$ are $R_3$,
x is 1
y is 1
z is 1
q is 0
m and j are 0, and
X is $^{18}$F or $^{123}$I.
13. A compound according to claim 12 wherein X is $^{123}$I.
14. A compound according to claim 1 wherein R1 and R2 are $R_3$,
x is 0
y is 1
z is 2
q is 1
m is 1
n is 1
j is 1, and
X is $^{18}$F, or $^{123}$I.
15. The compound of claim 14 wherein X is $^{123}$I.
16. A compound according to claim 1 wherein $R_1$ and $R_2$ are $R_3$,
x is 0
y is 1
z is 2
q is 0
m is 0
j is 1, and
X is $^{18}$F, or $^{123}$I.
17. The compound of claim 16 wherein X is $^{123}$I.
18. A compound according to claim 1 wherein R1 and R2 are $R_3$,
x is 0 or 1
y is 2
z is 4
q is 1
m is 1
n is 1
j is 1, and
X is $^{18}$F, or $^{123}$I.
19. The compound of claim 18 wherein X is $^{18}$F.
20. The compound of claim 18 wherein X is $^{123}$I.
21. A compound according to claim 1, wherein $R_1$ and $R_2$ are $R_3$,
x is 0 or 1
y is 2
z is 4
q is 0
m is 0
j is 1, and
X is $^{18}$F or $^{123}$I.
22. The compound of claim 21 wherein X is $^{18}$F.
23. The compound of claim 21 wherein X is $^{123}$I.
24. A compound of claim 1 wherein $R_1$ and $R_2$ are not $R_3$.
25. A compound according to claim 24 wherein X is $^{18}$F.
26. A compound according to claim 1 wherein $R_1$ is X—CH=CH—, $R_2$ is H, y is 1 and z is 2.
27. The compound of claim 26 wherein X is $^{123}$I.
28. The compound of claim 1, wherein $R_1$ is $^{18}$F, $R_2$ is H, y is 1, z is 2, and $R_4$ is —$CH_3$.
29. A method of in situ tumor imaging by positron emission tomography comprising:

administering to a subject suspected of having a tumor an image-generating amount of a compound according to claim 1, and measuring the distribution of the compound in the subject by positron emission tomography.

30. An amino acid analog having the general structure where $R_1$ is X, or $R_3$ $R_2$ is H, or $R_3$ if $R_1$ is $R_3$, such that is formed, where $R_4$ is $-(C_kH_{2k+1})$ where k is 3-5, and where $R_4$ is $-(C_kH_{2k-1})$ or $-(C_kH_{2k-3})$ where k=2-5 and where a is 1 to 5, x is 0 or 1, y is 1 or 2, z is 1, 2, 3 or 4 and z>y if y is 2, q is 1 or 0 if n is 1 and j is 0, n is 1 or 2, but 0 if m is 0, m is 0 or 1 j is 0, 1, 2 or 3 and

X is $^{18}F$, $^{123}I$, $^{124}I$, $^{125}I$, $^{131}I$, $^{75}Br$, $^{76}Br$, $^{77}Br$, $^{82}Br$, or At.

* * * * *